US012121578B2

(12) United States Patent
Yamaue et al.

(10) Patent No.: US 12,121,578 B2
(45) Date of Patent: Oct. 22, 2024

(54) RSV F/G CHIMERIC VACCINE

(71) Applicant: KM Biologics Co., Ltd., Kumamoto (JP)

(72) Inventors: Ryo Yamaue, Kikuchi (JP); Satoshi Kamakura, Kikuchi (JP); Mihoko Matsuo, Kikuchi (JP); Masaharu Torikai, Kikuchi (JP); Hiroaki Mori, Kikuchi (JP)

(73) Assignee: KM BIOLOGICS CO., LTD., Kumamoto (JP)

( * ) Notice: Subject to any disclaimer, the term of this patent is extended or adjusted under 35 U.S.C. 154(b) by 280 days.

(21) Appl. No.: 17/431,833

(22) PCT Filed: Feb. 27, 2020

(86) PCT No.: PCT/JP2020/008187
§ 371 (c)(1),
(2) Date: Aug. 18, 2021

(87) PCT Pub. No.: WO2020/175660
PCT Pub. Date: Sep. 3, 2020

(65) Prior Publication Data
US 2022/0111035 A1    Apr. 14, 2022

(30) Foreign Application Priority Data
Feb. 28, 2019    (JP) ................... 2019-036206

(51) Int. Cl.
*A61K 39/155*    (2006.01)
*A61P 31/14*    (2006.01)
*C12N 7/00*    (2006.01)
*C12N 15/62*    (2006.01)

(52) U.S. Cl.
CPC .......... *A61K 39/155* (2013.01); *A61P 31/14* (2018.01); *C12N 7/00* (2013.01); *C12N 15/62* (2013.01)

(58) Field of Classification Search
None
See application file for complete search history.

(56) References Cited

U.S. PATENT DOCUMENTS

| 2004/0175395 A1 | 9/2004 | Corvaia et al. |
| 2005/0164365 A1 | 7/2005 | Yonemura et al. |
| 2010/0203071 A1 | 8/2010 | Blais et al. |
| 2011/0154514 A1 | 6/2011 | Saito et al. |
| 2011/0177117 A1 | 7/2011 | Blais et al. |
| 2012/0093847 A1 | 4/2012 | Baudoux et al. |
| 2015/0166610 A1 | 6/2015 | Baudoux et al. |
| 2016/0046675 A1 | 2/2016 | Kwong et al. |

FOREIGN PATENT DOCUMENTS

| JP | 4150814 | 9/2008 |
| JP | 4310184 | 8/2009 |
| JP | 2010-522540 | 7/2010 |
| JP | 2011-528222 | 11/2011 |
| JP | 2012-530504 | 12/2012 |
| JP | 2808536 | 11/2015 |
| JP | 2016-519658 | 7/2016 |
| JP | 6162751 | 7/2017 |
| WO | 2009/055711 | 4/2009 |
| WO | 2009/148194 | 12/2009 |
| WO | 2010/077717 | 7/2010 |
| WO | 2016/144675 | 9/2016 |

OTHER PUBLICATIONS

Zheng et al., Front. Immunol., Sep. 2020, 11:526965, 15 pages. (Year: 2020).*
CHMP assessment report on Arexvy, European Medicines Agency, EMA/227054/2023, Apr. 2023, 103 pages. (Year: 2023).*
International Search Report issued May 26, 2020 in International (PCT) Application No. PCT/JP2020/008187.
Tang, Aimin et al., "A potent broadly neutralizing human RSV antibody targets conserved site IV of the fusion glycoprotein", 2019, Nature Communications, vol. 10, No. 1, pp. 1-13.
Shi, Ting et al., "Global, regional, and national disease burden estimates of acute lower respiratory infections due to respiratory syncytial virus in young children in 2015: a systematic review and modelling study", 2017, Lancet, vol. 390, pp. 946-958.
Mazur, Natalie I. et al., "The respiratory syncytial virus vaccine landscape: lessons from the graveyard and promising candidates", 2018, Lancet Infect. Dis., vol. 18, pp. e295-e311.
Johnson, Sara M. et al, "Respiratory Syncytial Virus Uses CX3CR1 as a Receptor on Primary Human Airway Epithelial Cultures", 2015, PLOS Pathogens, vol. 11, No. 12, pp. 1-16.
Fedechkin, Stanislav O. et al., "Structures of respiratory syncytial virus G antigen bound to broadly neutralizing antibodies", 2018, Science Immunology, vol. 3, No. 21, pp. 1-8.
Prince, Gregory A. et al., "Efficacy and Safety Studies of a Recombinant Chimeric Respiratory Syncytial Virus FG Glycoprotein Vaccine in Cotton Rats", 2000, J. Virology, vol. 74, No. 22, pp. 10287-10292.

(Continued)

*Primary Examiner* — Stacy B Chen
(74) *Attorney, Agent, or Firm* — WENDEROTH, LIND & PONACK, L.L.P.

(57) ABSTRACT

A novel vaccine antigen for prevention of Respiratory Syncytial Virus (RSV) infection is created which surpasses conventional vaccines comprising as an antigen RSV F protein alone in view of efficacy and/or safety. A vaccine is prepared which comprises as an antigen a RSV F/G chimeric protein wherein a portion of RSV F protein as a basic structure is replaced with a whole or a portion of Conserved Central Domain sequence of RSV G protein or wherein a whole or a portion of Conserved Central Domain sequence of RSV G is added to the basic structure. As a result of assessment of both efficacy and safety, a vaccine comprising as an antigen the F/G chimeric protein of the present invention confirmed to be more excellent than a vaccine comprising as an antigen RSV F protein alone in view of efficacy and/or safety.

27 Claims, 32 Drawing Sheets

Specification includes a Sequence Listing.

(56) References Cited

OTHER PUBLICATIONS

McLellan, Jason S. et al., "Structure of RSV Fusion Glycoprotein Trimer Bound to a Prefusion-Specific Neutralizing Antibody", 2013, Science, vol. 340, No. 6136, pp. 1113-1117.
"Anti-RS virus humanized monoclonal antibody preparation: SynagisR Solution for Intramuscular Administration", 2021, Astra-Zeneca, pp. 1-5, with partial English-language translation of relevant portion.
Han, Junyan et al., "Effects of Anti-G and Anti-F Antibodies on Airway Function after Respiratory Syncytial Virus Infection", 2014, American Journal of Respiratory Cell and Molecular Biology, vol. 51, No. 1, pp. 143-154.
"Virus Antibody Candidates", 2010, Trellis Bioscience, pp. 1-9, http://www.trellisbio.com/pipeline/viruses.html.
Boyoglu-Barnum, Seyhan et al., "Prophylaxis with a Respiratory Syncytial Virus (RSV) Anti-G Protein Monoclonal Antibody Shifts the Adaptive Immune Response to RSV rA2-line19F Infection from Th2 to Th1 in BALB/c Mice", 2014, J. Virology, vol. 88, No. 18, pp. 10569-10583.
Caidi, Hayat et al., "Anti-respiratory syncytial virus (RSV) G monoclonal antibodies reduce lung inflammation and viral lung titers when delivered therapeutically in a BALB/c mouse model", 2018, Antiviral Res. vol. 154, pp. 149-157.
Kim, Hyun Wha et al., "Respiratory Syncytial Virus Disease in Infants Despite Prior Administration of Antigenic Inactivated Vaccine", 1969, American Journal of Epidemiology, vol. 89, No. 4, pp. 422-434.
Johnson, Teresa R. et al., "Contribution of respiratory syncytial virus G antigenicity to vaccine-enhanced illness and the implications for severe disease during primary respiratory syncytial virus infection", 2004, Pediatric Infectious Disease Journal, vol. 23, Issue 1, pp. 1-37.
Moghaddam, Amin et al., "A potential molecular mechanism for hypersensitivity caused by formalin-inactivated vaccines", 2006, Nature Medicine, vol. 12, No. 8, pp. 1-4.
Delgado, Maria Florencia et al., "Lack of antibody affinity maturation due to poor Toll stimulation led to enhanced RSV disease", 2009, Nat. Med. vol. 15, No. 1, pp. 34-41.
Zhivaki, Dania et al., "Respiratory Syncytial Virus Infects Regulatory B Cells in Human Neonates via Chemokine Receptor CX3CR1 and Promotes Lung Disease Severity", 2017, Immunity, vol. 46, No. 2, pp. 301-314.
Schneider-Ohrum, Kirsten et al., "Immunization with Low Doses of Recombinant Postfusion or Prefusion Respiratory Syncytial Virus F Primes for Vaccine-Enhanced Disease in the Cotton Rat Model Independently of the Presence of a Th1-Biasing (GLA-SE) or Th2-Biasing (Alum) Adjuvant", 2017, J. Virology, vol. 91, Issue 8, pp. 1-19.
Elango, Narayanasamy et al., "Respiratory syncytial virus fusion glycoprotein: nucleotide sequence of mRNA, identification of cleavage activation site and amino acid sequence of N-terminus of F, Subunit", 1985, Nucleic Acids Research, vol. 13, No. 5, pp. 1559-1574.
Sullender, Wayne, "Antigenic Analysis of Chimeric and Truncated G Proteins of Respiratory Syncytial Virus", 1995, Virology, vol. 209, No. 1, pp. 70-79.
Yokoi, Hajime et al., "Detection and Subgrouping of Respiratory Syncytial Virus RNA by Real-time RT_PCR", 2012, Kansenshogaku Zasshi, vol. 86, No. 5, pp. 569-576.
Wu, Sheng-Jiun et al., "Characterization of the epitope for anti-human respiratory syncytial virus F protein monoclonal antibody 101F using synthetic peptides and genetic approaches", 2007, Journal of General Virology, vol. 88, pp. 2719-2723.
McLellan, Jason S. et al., "Structure of a Major Antigenic Site on the Respiratory Syncytial Virus Fusion Glycoprotein in Complex with Neutralizing Antibody 101F", 2010, J. Virology, vol. 84, No. 23, pp. 12236-12244.
Gilman, Morgan S. A. et al., "Rapid Profiling of RSV antibody repertoires from the memory B cells of naturally infected adult donors", 2016, Sci. Immunol, vol. 1, No. 6, pp. 1-21.
Tang, Aimin et al., "A potent broadly neutralizing human RSV antibody targets conserved site IV of the fusion glycoprotein", 2009, Nature Communications, vol. 10, No. 1, pp. 1-13.
International Preliminary Report on Patentability dated Sep. 2, 2021 in International (PCT) Application No. PCT/JP2020/008187.
Japanese Office Action issued on Nov. 15, 2022 in corresponding Japanese Patent Application No. 2021-502389 with machine translation.
Office Action and Search Report issued Aug. 26, 2023 in corresponding Chinese Application No. 202080017518.X, with English translations, 26 pages.
Extended European Search Report issued Sep. 12, 2022 in corresponding European Patent Application No. 20762080.8.
Office Action issued Dec. 22, 2023 in corresponding Korean Patent Application No. 10-2021-7029758, with English translation, 14 pages.

\* cited by examiner

| Protein names | Expression level (mg/L) |
|---|---|
| RSV F/G-A-1-0 | 1.67 |
| RSV F/G-A-1-1 | 10.00 |
| RSV F/G-A-1-2 | 9.00 |
| RSV F/G-A-1-3 | 2.72 |
| RSV F/G-A-2-0 | 3.50 |
| RSV F/G-A-2-1 | 13.00 |
| RSV F/G-A-2-2 | 10.00 |
| RSV F/G-A-2-3 | 6.67 |
| RSV F/G-A-3-0 | 10.50 |
| RSV F/G-A-3-1 | 30.33 |
| RSV F/G-A-3-2 | 29.33 |
| RSV F/G-A-3-3 | 6.67 |
| RSV F/G-A-4-0 | 0.55 |
| RSV F/G-A-4-1 | 3.44 |
| RSV F/G-A-4-2 | 2.12 |
| RSV F/G-A-6-0 | 6.44 |
| RSV F/G-A-6-1 | 23.23 |
| RSV F/G-A-6-2 | 18.20 |
| RSV F/G-A-7-0 | 10.40 |
| RSV F/G-A-7-1 | 13.33 |
| RSV F/G-A-7-2 | 15.47 |
| RSV F/G-A-8-0 | 3.56 |
| RSV F/G-A-8-1 | 18.23 |
| RSV F/G-A-8-2 | 11.47 |
| RSV F/G-A-5-0 | 0.67 |
| RSV F/G-A-5-1 | 2.77 |
| RSV F/G-A-5-2 | 1.40 |
| RSV F/G-A-5-3 | 1.64 |
| RSV F/G-A-9-0 Δ136aa | 7.33 |
| RSV F/G-A-9-4 Δ136aa | 42.67 |
| RSV F/G-A-9-1 Δ136aa | 35.67 |
| RSV F/G-A-9-2 Δ136aa | 27.00 |
| RSV F/G-A-9-3 Δ136aa | 4.17 |
| RSV wt F R136Q | 6.67 |
| RSV post F R136Q | 7.67 |
| RSV F/G-A-9-0 R136Q | 5.23 |
| RSV F/G-A-9-0 | 2.47 |
| RSV F/G-A-9-1 | 16.10 |
| RSV F/G-A-9-2 | 14.30 |
| RSV F/G-A-9-3 | 2.11 |
| RSV F/G-A-9-4 | 15.80

Fig. 6

| Protein names | Expression level (mg/L) |
|---|---|
| RSV F/G-A-10-0 | 3.64 |
| RSV F/G-A-10-1 | 8.96 |
| RSV F/G-A-10-2 | 11.85 |
| RSV F/G-A-11-0 | 5.03 |
| RSV F/G-A-11-1 | 11.14 |
| RSV F/G-A-11-2 | 10.48 |
| RSV F/G-A-10/10-0 | 2.44 |
| RSV F/G-A-10/10-1 | 4.63 |
| RSV F/G-A-10/10-2 | 3.50 |
| RSV F/G-A-11/11-0 | 3.43 |
| RSV F/G-A-11/11-1 | 7.00 |
| RSV F/G-A-11/11-2 | 6.57 |
| RSV F/G-A-12-0-010 | 8.57 |
| RSV F/G-A-12-0-020 | 6.47 |
| RSV F/G-A-12-0-030 | 9.14 |
| RSV F/G-A-12-0-040 | 7.24 |
| RSV F/G-A-13-0-020 | 9.50 |
| RSV F/G-A-13-0-030 | 7.11 |
| RSV F/G-A-13-0-040 | 4.43 |
| RSV F/G-A-13-0-141 | 18.97 |
| RSV F/G-A-12-0-111 | 7.71 |
| RSV F/G-A-13-0-111 | 16.79 |
| RSV F/G-A-14-0-G/EGE/G | 8.64 |
| RSV F/G-A-14-0-G/GEG/G | 7.92 |
| RSV F/G-A-14-0-G/EGEG/G | 6.84 |
| RSV F/G-A-14-0-G/GEEG/G | 8.11 |
| RSV F/G-A-14-0-E/GEG/E | 9.72 |
| RSV F/G-A-14-0-E/EGEG/E | 11.00 |
| RSV F/G-A-14-0-E/GEGE/E | 9.50 |
| RSV F/G-A-14-0-E/EGGE/E | 15.32 |
| RSV F/G-A-14-0-E/GEEG/E | 18.20 |
| RSV F/G-A-17-0-E/E/E/E | 6.49 |
| RSV F/G-A-17-0-E/G/G/E | 5.60 |
| RSV F/G-A-17-0-G/G/G/G | 3.56 |
| RSV F/G-A-18-0-G

Fig. 10

| Lane No. | Sample |
|---|---|
| 1 | Marker |
| 2 | RSV pre F |
| 3 | RSV post F |
| 4 | RSV WT |
| 5 | RSV F/G-A-9-2 |
| 6 | RSV F/G-A-7-2 |
| 7 | RSV F/G-A-9-0 |
| 8 | RSV F/G-A-8-1 |
| 9 | RSV F/G-A-8-2 |
| 10 | RSV F/G-A-9-0 |
| 11 | RSV F/G-A-9-1 |
| 12 | RSV F/G-A-9-2 |
| 13 | RSV F/G-A-9-3 |
| 14 | RSV F/G-A-9-0 Δ136aa |
| 15 | RSV F/G-A-9-4 Δ136aa |

Fig. 11

| Lane No. | Sample |
|---|---|
| 1 | Marker |
| 2 | RSV pre F |
| 3 | RSV post F |
| 4 | RSV WT |
| 5 | RSV F/G-A-9-2 |
| 6 | RSV F/G-A-9-1 Δ136aa |
| 7 | RSV F/G-A-9-2 Δ136aa |
| 8 | RSV F/G-A-9-3 Δ136aa |
| 9 | RSV WT F R13Q |
| 10 | RSV post F R13Q |
| 11 | RSV F/G-A-9-0 R13Q |
| 12 | RSV F/G-A-9-0 |
| 13 | RSV F/G-A-9-4 |
| 14 | RSV F/G-A-9-3 |
| 15 | RSV F/G-A-9-1 |

Fig. 16

RSV post F | RSV pre F

RSV F/G-A-9-1 | RSV F/G-A-9-2

Fig. 17

| Protein names | Absorbance (antigeninc site mAbs) | | | | |
|---|---|---|---|---|---|
| | site 0 | site I | site II | site III | site IV |
| RSV F/G-A-1-0 | 3.60 | 1.08 | 2.18 | 1.35 | 1.21 |
| RSV F/G-A-1-1 | 3.43 | 1.76 | 2.94 | 1.82 | 0.08 |
| RSV F/G-A-1-2 | 3.57 | 1.87 | 3.00 | 1.78 | 1.11 |
| RSV F/G-A-1-3 | 3.37 | 0.37 | 1.34 | 1.18 | 0.07 |
| RSV F/G-A-2-0 | 3.58 | 1.22 | 2.36 | 1.51 | 1.58 |
| RSV F/G-A-2-1 | 2.90 | 1.69 | 2.88 | 1.70 | 0.07 |
| RSV F/G-A-2-2 | 2.78 | 1.81 | 3.00 | 1.75 | 0.59 |
| RSV F/G-A-2-3 | 3.46 | 0.79 | 2.46 | 1.48 | 0.10 |
| RSV F/G-A-3-0 | 2.36 | 1.97 | 3.14 | 1.98 | 3.56 |
| RSV F/G-A-3-1 | 2.01 | 1.96 | 2.98 | 1.84 | 0.06 |
| RSV F/G-A-3-2 | 2.05 | 1.85 | 2.92 | 1.80 | 1.39 |
| RSV F/G-A-3-3 | 1.53 | 1.00 | 1.97 | 1.35 | 0.05 |
| RSV F/G-A-4-0 | 0.09 | 0.14 | 0.04 | 0.18 | 0.14 |
| RSV F/G-A-4-1 | 0.20 | 1.04 | 1.44 | 0.47 | 0.05 |
| RSV F/G-A-4-2 | 0.26 | 0.89 | 1.45 | 0.59 | 0.21 |
| RSV F/G-A-6-0 | 3.63 | 1.98 | 3.36 | 1.66 | 3.52 |
| RSV F/G-A-6-1 | 3.63 | 1.99 | 3.18 | 2.06 | 0.09 |
| RSV F/G-A-6-2 | 3.33 | 1.82 | 3.26 | 1.95 | 1.45 |
| RSV F/G-A-7-0 | 3.10 | 2.04 | 3.17 | 1.84 | 3.52 |
| RSV F/G-A-7-1 | 3.06 | 1.85 | 3.24 | 1.91 | 0.07 |
| RSV F/G-A-7-2 | 2.67 | 1.79 | 3.09 | 1.92 | 2.21 |
| RSV F/G-A-8-0 | 2.21 | 0.78 | 0.93 | 1.05 | 1.32 |
| RSV F/G-A-8-1 | 2.17 | 1.39 | 2.45 | 1.48 | 0.08 |
| RSV F/G-A-8-2 | 2.02 | 1.32 | 2.19 | 1.25 | 0.49 |
| RSV F/G-A-5-1 | 1.72 | 0.95 | 1.57 | 1.27 | 0.09 |
| RSV F/G-A-5-2 | 1.72 | 0.79 | 1.64 | 1.16 | 0.29 |
| RSV F/G-A-5-3 | 2.04 | 0.33 | 0.60 | 0.68 | 0.09 |
| RSV F/G-A-9-0 Δ136aa | 2.37 | 1.78 | 2.72 | 1.89 | 3.17 |
| RSV F/G-A-9-4 Δ136aa | 2.08 | 1.79 | 2.91 | 1.94 | 0.13 |
| RSV F/G-A-9-1 Δ136aa | 2.38 | 1.75 | 3.07 | 2.16 | 0.08 |
| RSV F/G-A-9-2 Δ136aa | 2.27 | 1.88 | 3.11 | 2.21 | 1.46 |
| RSV F/G-A-9-3 Δ136aa | 2.05 | 1.10 | 2.09 | 1.45 | 0.10 |
| RSV wt F R136Q | 1.84 | 1.00 | 1.30 | 1.57 | 1.80 |
| RSV post F R136Q | 0.25 | 1.87 | 2.61 | 2.15 | 3.52 |
| RSV F/G-A-9-0 R136Q | 3.51 | 2.09 | 3.17 | 2.30 | 3.68 |
| RSV F/G-A-9-0 | 0.62 | 0.53 | 1.25 | 0.89 | 0.81 |
| RSV F/G-A-9-4 | 1.19 | 1.44 | 2.10 | 1.51 | 0.09 |
| RSV F/G-A-9-3 | 0.28 | 0.25 | 0.32 | 0.51 | 0.10 |
| RSV F/G-A-9-1 | 0.42 | 1.51 | 2.05 | 0.98 | 0.10 |
| RSV F/G-A-9-2 | 0.42 | 1.43 | 2.27 | 0.98 | 0.47 |
| RSV pre F | 3.75 | 1.30 | 3.69 | 2.85 | 3.57 |
| RSV post F | 0.15 | 1.85 | 2.28 | 1.92 | 2.21 |
| RSV wt F | 0.52 | 1.47 |  | 1.25 | 1.38 |
| Saline | 0.05 | 0.06 |  | 0.10 | 0.09 |

Fig. 18

| Protein names | Absorbance (antigenic site mAbs) | | | | |
|---|---|---|---|---|---|
| | siteΦ | site I | site II | site III | site IV |
| RSV F/G-A-10-0 | 3.48 | 1.74 | 2.89 | 2.17 | 3.45 |
| RSV F/G-A-10-1 | 3.58 | 2.06 | 3.13 | 2.16 | 0.09 |
| RSV F/G-A-10-2 | 3.14 | 2.00 | 3.15 | 1.88 | 2.86 |
| RSV F/G-A-11-0 | 3.45 | 2.38 | 3.09 | 2.15 | 3.64 |
| RSV F/G-A-11-1 | 3.00 | 2.23 | 3.20 | 2.16 | 0.09 |
| RSV F/G-A-11-2 | 2.96 | 2.15 | 3.21 | 1.92 | 3.46 |
| RSV F/G-A-10/10-0 | 2.76 | 0.28 | 0.30 | 0.79 | 1.00 |
| RSV F/G-A-10/10-1 | 3.48 | 1.12 | 3.09 | 1.83 | 0.10 |
| RSV F/G-A-10/10-2 | 3.50 | 0.94 | 2.60 | 2.07 | 1.47 |
| RSV F/G-A-11/11-0 | 3.47 | 1.40 | 2.40 | 2.07 | 3.37 |
| RSV F/G-A-11/11-1 | 3.62 | 1.70 | 3.43 | 2.51 | 0.09 |
| RSV F/G-A-11/11-2 | 3.49 | 1.67 | 3.40 | 2.55 | 3.33 |
| RSV F/G-A-12-0-010 | 3.40 | 1.85 | 3.29 | 2.35 | 3.35 |
| RSV F/G-A-12-0-020 | 3.30 | 1.69 | 3.33 | 2.26 | 3.35 |
| RSV F/G-A-12-0-030 | 3.35 | 1.79 | 3.24 | 2.03 | 3.39 |
| RSV F/G-A-12-0-040 | 3.39 | 1.86 | 3.18 | 2.07 | 3.32 |
| RSV F/G-A-13-0-020 | 3.72 | 1.94 | 3.20 | 2.39 | 3.36 |
| RSV F/G-A-13-0-030 | 3.61 | 2.01 | 3.07 | 2.32 | 3.94 |
| RSV F/G-A-13-0-040 | 4.00 | 1.83 | 3.35 | 2.27 | 3.52 |
| RSV F/G-A-13-0-141 | 3.55 | 1.76 | 3.36 | 2.00 | 3.44 |
| RSV F/G-A-12-0-111 | 3.50 | 1.75 | 3.13 | 2.26 | 3.88 |
| RSV F/G-A-13-0-111 | 3.73 | 2.00 | 3.17 | 2.13 | 3.54 |
| RSV F/G-A-14-0-G/EGE/G | 3.56 | 1.90 | 3.16 | 2.32 | 3.20 |
| RSV F/G-A-14-0-G/GEG/G | 3.51 | 2.05 | 3.24 | 2.48 | 3.72 |
| RSV F/G-A-14-0-G/EGEG/G | 3.68 | 1.91 | 3.06 | 2.22 | 3.49 |
| RSV F/G-A-14-0-G/GEEG/G | 3.66 | 2.02 | 3.00 | 2.32 | 3.55 |
| RSV F/G-A-14-0-E/GEG/E | 3.65 | 1.96 | 2.97 | 2.35 | 3.63 |
| RSV F/G-A-14-0-E/EGEG/E | 3.47 | 1.91 | 2.87 | 2.26 | 3.80 |
| RSV F/G-A-14-0-E/GEGE/E | 3.56 | 1.74 | 2.93 | 2.31 | 3.52 |
| RSV F/G-A-14-0-E/EGGE/E | 3.52 | 1.80 | 2.99 | 2.26 | 3.63 |
| RSV F/G-A-14-0-E/GEEG/E | 3.58 | 1.83 | 3.05 | 2.24 | 3.58 |
| RSV F/G-A-17-0-E/E/E/E | 3.55 | 1.55 | 2.66 | 2.23 | 2.65 |
| RSV F/G-A-17-0-E/G/G/E | 3.47 | 1.80 | 2.84 | 2.43 | 2.66 |
| RSV F/G-A-17-0-G/G/G/G | 3.74 | 1.21 | 2.45 | 2.39 | 2.60 |
| RSV F/G-A-18-0-G/E/E/G | 0.10 | 0.06 | 0.05 | 0.12 | 0.10 |
| RSV pre F | 3.58 | 1.65 | 3.04 | 2.77 | 3.82 |
| RSV wt F | 0.57 | 1.46 | 2.07 | 1.22 | 3.46 |
| RSV post F | 0.15 | 1.76 | 2.21 | 1.55 | 3.41 |
| RSV F/G-A-9-2 | 0.73 | 1.31 | 1.82 | 1.19 | 1.00 |
| Saline | 0.08 | 0.10 | 0.06 | 0.13 | 0.11 |

Fig. 28

| Lane No. | Sample |
|---|---|
| 1 | Marker |
| 2 | RSV pre F |
| 3 | RSV post F |
| 4 | RSV F/G-A-11/11-0 |
| 5 | RSV F/G-A-11/11-1 |
| 6 | RSV F/G-A-11/11-2 |
| 7 | RSV F/G-A-12-0-048 |
| 8 | RSV F/G-A-13-0-030 |
| 9 | RSV F/G-A-13-0-048 |
| 10 | RSV F/G-A-14-0-G/G/GE/G |
| 11 | RSV F/G-A-17-0-E/E/E/E |
| 12 | RSV F/G-A-17-0-G/G/E |
| 13 | RSV F/G-A-17-0-G/G/G/G |
| 14 | RSV F/G-A-18-0-G/G/E/G |
| 15 | RSV F/G-A-18-0-G/G/G/G |

Fig. 29

| Lane No. | Sample |
|---|---|
| 1 | Marker |
| 2 | RSV pre F |
| 3 | RSV post F |
| 4 | RSV F/G-A-1-2.seq11 |
| 5 | RSV F/G-A-1-2.N191S |
| 6 | RSV F/G-A-1-2.K197R |
| 7 | RSV F/G-A-2-2.seq11 |
| 8 | RSV F/G-A-2-2.N191S |
| 9 | RSV F/G-A-2-2.K197R |
| 10 | RSV F/G-A-9-2.seq11 |
| 11 | RSV F/G-A-9-2.D160H |
| 12 | RSV F/G-A-7-2.seq11 |

Fig. 34

| Lane No. | Sample |
|---|---|
| 1 | Marker |
| 2 | RSV pre F |
| 3 | RSV post F |
| 4 | RSV F/G-A-17-2-E/G/G/E_seq11 |
| 5 | RSV F/G-A-17-2-G/G/G/G_seq11 |
| 6 | RSV F/G-D-1-0_seq11 |
| 7 | RSV F/G-D-2-0 |
| 8 | RSV F/G-D-2-0_seq11 |
| 9 | RSV F/G-D-3-0 |
| 10 | RSV F/G-D-4-0 |
| 11 | RSV F/G-D-5-0 |
| 12 | RSV F/G-D-6-0 |

Fig. 35

| Lane No. | Sample |
|---|---|
| 1 | Marker |
| 2 | RSV pre F |
| 3 | RSV post F |
| 4 | RSV F/G-D-7-0 |
| 5 | RSV F/G-D-8-0 |
| 6 | RSV F/G-D-9-0 |
| 7 | RSV F/G-D-1-2 |
| 8 | RSV F/G-D-1-2_seq11 |
| 9 | RSV F/G-D-2-2 |
| 10 | RSV F/G-D-2-2_seq11 |
| 11 | RSV F/G-D-9-2 |
| 12 | RSV F/G-D-10-0 |

| Protein names | Absorbance (antigeninc site mAbs) | | | | |
|---|---|---|---|---|---|
| | site 0 | site I | site II | site III | site IV |
| RSV F/G-A-1-2_seq11 | 0.84 | 0.99 | 2.47 | 1.36 | 0.77 |
| RSV F/G-A-1-2_N191S | 1.33 | 1.08 | 2.27 | 1.58 | 0.67 |
| RSV F/G-A-1-2_K197R | 1.54 | 1.07 | 2.31 | 1.45 | 0.62 |
| RSV F/G-A-2-2_seq11 | 0.67 | 0.97 | 1.89 | 1.41 | 0.52 |
| RSV F/G-A-2-2_N191S | 0.88 | 0.82 | 1.91 | 1.25 | 0.36 |
| RSV F/G-A-2-2_K197R | 0.79 | 0.94 | 1.87 | 1.27 | 0.44 |
| RSV F/G-A-9-2_seq11 | 0.26 | 0.79 | 1.73 | 0.94 | 0.35 |
| RSV F/G-A-9-2_D162H | 0.20 | 0.68 | 1.55 | 0.92 | 0.33 |
| RSV F/G-A-7-2_seq11 | 1.03 | 1.55 | 2.99 | 1.78 | 1.77 |
| RSV F/G-A-7-2_N191S | 0.90 | 1.50 | 3.11 | 1.79 | 2.10 |
| RSV F/G-A-7-2_K197R | 1.12 | 1.49 | 3.09 | 1.80 | 2.23 |
| RSV F/G-A-10-2_seq11 | 1.52 | 1.52 | 2.95 | 1.97 | 2.16 |
| RSV F/G-A-10-2_D162H/N191S | 0.93 | 1.27 | 2.38 | 1.44 | 0.79 |
| RSV F/G-A-10-2_D162H/K197R | 0.93 | 1.17 | 2.43 | 1.36 | 0.66 |
| RSV F/G-A-12-0-010_seq11 | 1.33 | 1.33 | 2.39 | 1.62 | 3.13 |
| RSV F/G-A-13-0-010_seq11 | 1.34 | 1.39 | 2.96 | 1.96 | 3.39 |
| RSV F/G-A-12-0-111_seq11 | 2.22 | 1.69 | 2.54 | 1.25 | 3.19 |
| RSV F/G-A-13-0-111_seq11 | 2.75 | 1.99 | 2.90 | 1.58 | 3.16 |
| RSV F/G-A-14-0-G/EGE/G_seq11 | 2.82 | 2.17 | 3.15 | 1.72 | 3.62 |
| RSV F/G-A-14-0-E/GEG/E_seq11 | 2.63 | 1.76 | 2.70 | 1.56 | 3.21 |
| RSV F/G-A-14-0-E/EGGE/E_seq11 | 2.66 | 1.74 | 3.09 | 1.70 | 3.26 |
| RSV F/G-A-14-0-E/GEEG/E_seq11 | 2.81 | 1.77 | 2.92 | 1.58 | 3.51 |
| RSV F/G-A-17-0-E/E/E/E_seq11 | 1.85 | 0.68 | 0.94 | 1.02 | 1.28 |
| RSV F/G-A-17-0-E/G/G/E_seq11 | 1.96 | 1.20 | 1.80 | 1.04 | 2.29 |
| RSV F/G-A-17-0-G/G/G/G_seq11 | 1.23 | 0.53 | 0.66 | 0.89 | 1.05 |
| RSV F/G-A-12-2-010_seq11 | 1.41 | 1.60 | 2.74 | 1.14 | 1.67 |
| RSV F/G-A-13-2-010_seq11 | 2.88 | 2.19 | 3.31 | 2.04 | 3.37 |
| RSV F/G-A-12-2-111_seq11 | 2.38 | 1.96 | 3.26 | 1.72 | 2.78 |
| RSV F/G-A-13-2-111_seq11 | 2.17 | 1.86 | 3.27 | 2.18 | 2.98 |
| RSV F/G-A-14-2-G/EGE/G_seq11 | 1.83 | 2.02 | 3.09 | 1.94 | 2.70 |
| RSV F/G-A-14-2-E/GEG/E_seq11 | 2.26 | 1.92 | 3.19 | 1.75 | 2.84 |
| RSV F/G-A-14-2-E/EGGE/E_seq11 | 2.00 | 1.94 | 3.32 | 1.75 | 3.20 |
| RSV F/G-A-14-2-E/GEEG/E_seq11 | 2.31 | 2.14 | 3.56 | 2.13 | 2.83 |
| RSV F/G-A-17-2-E/E/E/E_seq11 | 2.85 | 2.25 | 3.97 | 2.25 | 2.68 |
| RSV F/G-A-17-2-E/G/G/E_seq11 | 1.91 | 1.87 | 3.98 | 2.09 | 2.26 |
| RSV F/G-A-17-2-G/G/G/G_seq11 | 2.42 | 1.68 | 3.53 | 1.97 | 1.83 |
| RSV pre F | 3.62 | 1.48 | 3.80 | 2.83 | 3.62 |
| RSV wt F | 0.78 | 1.45 | 2.96 | 1.84 | 2.99 |
| RSV post F | 0.19 | 1.54 | 2.95 | 1.18 | 3.03 |
| Saline | 0.05 | 0.07 | 0.09 | 0.29 | 0.05 |

Fig. 41

| Protein names | Absorbance (antigenic site mAbs) | | | | |
|---|---|---|---|---|---|
| | site Ø | site I | site II | site III | site IV |
| RSV F/G-D-1-0 | 1.55 | 2.03 | 3.44 | 0.74 | 2.99 |
| RSV F/G-D-1-0_seq11 | 2.01 | 2.22 | 3.52 | 1.52 | 3.44 |
| RSV F/G-D-2-0 | 0.41 | 0.70 | 0.52 | 0.33 | 1.23 |
| RSV F/G-D-2-0_seq11 | 0.53 | 1.27 | 1.18 | 0.52 | 2.42 |
| RSV F/G-D-3-0 | 0.43 | 0.65 | 0.35 | 0.28 | 0.58 |
| RSV F/G-D-4-0 | 0.12 | 0.08 | 0.14 | 0.09 | 0.15 |
| RSV F/G-D-5-0 | 0.23 | 0.15 | 0.13 | 0.22 | 0.20 |
| RSV F/G-D-6-0 | 2.20 | 1.94 | 3.46 | 1.79 | 3.62 |
| RSV F/G-D-7-0 | 1.22 | 2.23 | 3.40 | 2.57 | 3.66 |
| RSV F/G-D-8-0 | 1.04 | 1.06 | 1.39 | 0.98 | 1.73 |
| RSV F/G-D-9-0 | 0.21 | 0.23 | 0.09 | 0.09 | 0.11 |
| RSV F/G-D-1-2 | 1.78 | 2.03 | 3.39 | 1.13 | 2.46 |
| RSV F/G-D-1-2_seq11 | 1.91 | 2.22 | 3.49 | 1.54 | 2.70 |
| RSV F/G-D-2-2 | 0.76 | 2.28 | 3.32 | 1.30 | 0.07 |
| RSV F/G-D-2-2_seq11 | 1.88 | 2.08 | 3.53 | 1.06 | 0.08 |
| RSV F/G-D-9-2 | 0.64 | 1.52 | 3.01 | 0.86 | 0.08 |
| RSV F/G-D-10-0 | 0.91 | 2.12 | 3.53 | 1.55 | 3.46 |
| RSV F/G-D-11-0 | 1.08 | 2.07 | 3.61 | 1.71 | 3.47 |
| RSV F/G-D-12-0-010 | 1.04 | 1.85 | 3.57 | 1.67 | 3.55 |
| RSV F/G-D-12-0-040 | 1.17 | 2.13 | 3.47 | 1.32 | 3.53 |
| RSV F/G-D-13-0-010 | 1.16 | 1.97 | 3.54 | 1.98 | 3.41 |
| RSV F/G-D-13-0-040 | 1.07 | 1.94 | 3.48 | 1.79 | 3.56 |
| RSV F/G-D-14-0-G/G/G | 1.68 | 2.18 | 3.52 | 2.01 | 3.54 |
| RSV F/G-D-14-0-E/E/E | 1.67 | 2.26 | 3.55 | 2.02 | 3.63 |
| RSV F/G-D-14-0-G/GEG/G | 1.59 | 2.16 | 3.58 | 1.85 | 3.64 |
| RSV F/G-D-14-0-G/EGE/G | 1.11 | 2.19 | 3.48 | 2.05 | 3.73 |
| RSV F/G-D-14-0-E/EGE/E | 1.20 | 2.13 | 3.49 | 1.86 | 3.53 |
| RSV F/G-D-14-0-E/GEG/E | 1.28 | 2.20 | 3.33 | 1.99 | 3.49 |
| RSV F/G-D-14-0-E/EGEG/E | 0.34 | 2.01 | 3.29 | 1.06 | 3.61 |
| RSV F/G-D-14-0-E/GEGE/E | 0.97 | 2.02 | 3.39 | 1.81 | 3.54 |
| RSV F/G-D-14-0-E/EGGE/E | 0.89 | 2.48 | 3.52 | 1.68 | 3.46 |
| RSV F/G-D-14-0-E/GEEG/E | 1.23 | 2.35 | 3.48 | 2.03 | 3.48 |
| RSV F/G-AD-9/9-0 | 0.05 | 0.05 | 0.07 | 0.07 | 0.07 |
| RSV F/G-AD-9/9-1 | 0.07 | 0.06 | 0.09 | 0.08 | 0.09 |
| RSV F/G-AD-9/9-2 | 0.10 | 0.08 | 0.10 | 0.11 | 0.10 |
| RSV F/G-AD-7/9-0 | 0.32 | 0.09 | 0.13 | 0.18 | 0.20 |
| RSV F/G-AD-7/9-1 | 1.30 | 0.46 | 1.08 | 0.62 | 0.10 |
| RSV F/G-AD-7/9-2 | 1.39 | 0.66 | 1.56 | 0.69 | 0.38 |
| RSV F/G-AD-9/7-0 | 1.42 | 0.93 | 1.70 | 1.28 | 2.88 |
| RSV F/G-AD-9/7-1 | 1.04 | 1.23 | 2.61 | 1.39 | 0.10 |
| RSV F/G-AD-9/7-2 | 0.78 | 1.30 | 2.09 | 1.05 | 0.59 |
| RSV F/G-AD-7/7-0 | 1.59 | 1.03 | 1.41 | 1.06 | 2.31 |
| RSV F/G-AD-7/7-1 | 1.78 | 1.42 | 2.81 | 1.36 | 0.09 |
| RSV F/G-AD-7/7-2 | 1.87 | 1.96 | 3.36 | 1.94 | 2.77 |
| RSV F/G-B-8-1 | 1.48 | 0.08 | 3.22 | 1.86 | 0.10 |
| RSV F/G-B-8-2 | 1.25 | 0.07 | 3.30 | 1.76 | 1.31 |
| RSV pre F | 3.62 | 1.48 | 3.60 | 2.63 | 3.62 |
| RSV wt F | 0.78 | 1.45 | 2.98 | 1.84 | 2.99 |
| RSV post F | 0.19 | 1.54 | 2.99 | 1.18 | 3.03 |
| Saline | 0.05 | 0.07 | 0.09 | 0.29 | 0.05 |

Fig. 42

SEQUENCE LISTING

```
<160> NUMBER OF SEQ ID NOS: 11

<210> SEQ ID NO 1
<211> LENGTH: 513
<212> TYPE: PRT
<213> ORGANISM: respiratory syncytial virus

<400> SEQUENCE: 1

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240
```

```
Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Phe Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu
```

<210> SEQ ID NO 2
<211> LENGTH: 298
<212> TYPE: PRT
<213> ORGANISM: respiratory syncytial virus

<400> SEQUENCE: 2

```
Met Ser Lys Asn Lys Asp Gln Arg Thr Ala Lys Thr Leu Glu Arg Thr
1               5                   10                  15

Trp Asp Thr Leu Asn His Leu Leu Phe Ile Ser Ser Cys Leu Tyr Lys
                20                  25                  30

Leu Asn Leu Lys Ser Val Ala Gln Ile Thr Leu Ser Ile Leu Ala Met
            35                  40                  45

Ile Ile Ser Thr Ser Leu Ile Ile Ala Ala Ile Phe Ile Ala Ser
    50                  55                  60

Ala Asn His Lys Val Thr Pro Thr Thr Ala Ile Ile Gln Asp Ala Thr
65                  70                  75                  80

Ser Gln Ile Lys Asn Thr Thr Pro Thr Tyr Leu Thr Gln Asn Pro Gln
                85                  90                  95
```

-continued

```
Leu Gly Ile Ser Pro Ser Asn Pro Ser Glu Ile Thr Ser Gln Ile Thr
            100                 105                 110

Thr Ile Leu Ala Ser Thr Thr Pro Gly Val Lys Ser Thr Leu Gln Ser
        115                 120                 125

Thr Thr Val Lys Thr Lys Asn Thr Thr Thr Thr Gln Thr Gln Pro Ser
    130                 135                 140

Lys Pro Thr Thr Lys Gln Arg Gln Asn Lys Pro Pro Ser Lys Pro Asn
145                 150                 155                 160

Asn Asp Phe His Phe Glu Val Phe Asn Phe Val Pro Cys Ser Ile Cys
                165                 170                 175

Ser Asn Asn Pro Thr Cys Trp Ala Ile Cys Lys Arg Ile Pro Asn Lys
            180                 185                 190

Lys Pro Gly Lys Lys Thr Thr Thr Lys Pro Thr Lys Lys Pro Thr Leu
        195                 200                 205

Lys Thr Thr Lys Lys Asp Pro Lys Pro Gln Thr Thr Lys Ser Lys Glu
    210                 215                 220

Val Pro Thr Thr Lys Pro Thr Glu Glu Pro Thr Ile Asn Thr Thr Lys
225                 230                 235                 240

Thr Asn Ile Ile Thr Thr Leu Leu Thr Ser Asn Thr Thr Gly Asn Pro
                245                 250                 255

Glu Leu Thr Ser Gln Met Glu Thr Phe His Ser Thr Ser Ser Glu Gly
            260                 265                 270

Asn Pro Ser Pro Ser Gln Val Ser Thr Thr Ser Glu Tyr Pro Ser Gln
        275                 280                 285

Pro Ser Ser Pro Pro Asn Thr Pro Arg Gln
    290                 295

<210> SEQ ID NO 3
<211> LENGTH: 513
<212> TYPE: PRT
<213> ORGANISM: respiratory syncytial virus

<400> SEQUENCE: 3

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
                20                  25                  30

Tyr Gln Ser Thr Cys Ser Ala Val Ser Lys Gly Tyr Leu Ser Ala Leu
            35                  40                  45

Arg Thr Gly Trp Tyr Thr Ser Val Ile Thr Ile Glu Leu Ser Asn Ile
        50                  55                  60

Lys Lys Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175
```

```
Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
            195                 200                 205

Lys Gln Ser Cys Ser Ile Ser Asn Ile Glu Thr Val Ile Glu Phe Gln
            210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
            245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
            275                 280                 285

Met Ser Ile Ile Lys Glu Glu Val Leu Ala Tyr Val Val Gln Leu Pro
            290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
            325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
            355                 360                 365

Thr Met Asn Ser Leu Thr Leu Pro Ser Glu Val Asn Leu Cys Asn Val
            370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
            405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Gln Glu Gly
            450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
            485                 490                 495

Glu Lys Ile Asn Gln Ser Leu Ala Phe Ile Arg Lys Ser Asp Glu Leu
            500                 505                 510

Leu

<210> SEQ ID NO 4
<211> LENGTH: 513
<212> TYPE: PRT
<213> ORGANISM: respiratory syncytial virus

<400> SEQUENCE: 4

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30
```

-continued

```
Tyr Gln Ser Thr Cys Ser Ala Val Ser Lys Gly Tyr Leu Ser Ala Leu
         35                  40                  45

Arg Thr Gly Trp Tyr Thr Ser Val Ile Thr Ile Glu Leu Ser Asn Ile
 50                  55                  60

Lys Glu Asn Lys Cys Asn Gly Thr Asp Ala Lys Val Lys Leu Ile Lys
 65                  70                  75                  80

Gln Glu Leu Asp Lys Tyr Lys Asn Ala Val Thr Glu Leu Gln Leu Leu
                 85                  90                  95

Met Gln Ser Thr Pro Ala Thr Asn Asn Arg Ala Arg Arg Glu Leu Pro
             100                 105                 110

Arg Phe Met Asn Tyr Thr Leu Asn Asn Ala Lys Lys Thr Asn Val Thr
             115                 120                 125

Leu Ser Lys Lys Arg Lys Arg Arg Phe Leu Gly Phe Leu Leu Gly Val
130                 135                 140

Gly Ser Ala Ile Ala Ser Gly Val Ala Val Cys Lys Val Leu His Leu
145                 150                 155                 160

Glu Gly Glu Val Asn Lys Ile Lys Ser Ala Leu Leu Ser Thr Asn Lys
                 165                 170                 175

Ala Val Val Ser Leu Ser Asn Gly Val Ser Val Leu Thr Phe Lys Val
             180                 185                 190

Leu Asp Leu Lys Asn Tyr Ile Asp Lys Gln Leu Leu Pro Ile Leu Asn
             195                 200                 205

Lys Gln Ser Cys Ser Ile Ser Asn Ile Glu Thr Val Ile Glu Phe Gln
             210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                 245                 250                 255

Leu Leu Ser Leu Ile Asn Asp Met Pro Ile Thr Asn Asp Gln Lys Lys
             260                 265                 270

Leu Met Ser Asn Asn Val Gln Ile Val Arg Gln Gln Ser Tyr Ser Ile
             275                 280                 285

Met Cys Ile Ile Lys Glu Glu Val Leu Ala Tyr Val Val Gln Leu Pro
290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                 325                 330                 335

Thr Asp Arg Gly Trp Tyr Cys Asp Asn Ala Gly Ser Val Ser Phe Phe
             340                 345                 350

Pro Gln Ala Glu Thr Cys Lys Val Gln Ser Asn Arg Val Phe Cys Asp
             355                 360                 365

Thr Met Asn Ser Leu Thr Leu Pro Ser Glu Val Asn Leu Cys Asn Val
370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                 405                 410                 415

Tyr Gly Lys Thr Lys Cys Thr Ala Ser Asn Lys Asn Arg Gly Ile Ile
             420                 425                 430

Lys Thr Phe Ser Asn Gly Cys Asp Tyr Val Ser Asn Lys Gly Val Asp
             435                 440                 445
```

-continued

```
Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480
Leu Val Phe Pro Ser Asp Glu Phe Asp Ala Ser Ile Ser Gln Val Asn
                485                 490                 495
Glu Lys Ile Asn Gln Ser Leu Ala Phe Ile Arg Lys Ser Asp Glu Leu
            500                 505                 510
Leu

<210> SEQ ID NO 5
<211> LENGTH: 5
<212> TYPE: PRT
<213> ORGANISM: Artificial Sequence
<220> FEATURE:
<223> OTHER INFORMATION: Linker 1

<400> SEQUENCE: 5

Gly Gly Gly Gly Ser
1               5

<210> SEQ ID NO 6
<211> LENGTH: 5
<212> TYPE: PRT
<213> ORGANISM: Artificial Sequence
<220> FEATURE:
<223> OTHER INFORMATION: Linker 2

<400> SEQUENCE: 6

Glu Ala Ala Ala Lys
1               5

<210> SEQ ID NO 7
<211> LENGTH: 23
<212> TYPE: DNA
<213> ORGANISM: Artificial Sequence
<220> FEATURE:
<223> OTHER INFORMATION: sense primer - RSVf-F

<400> SEQUENCE: 7
carcaaagtt aytctatcat gtc                                              23

<210> SEQ ID NO 8
<211> LENGTH: 23
<212> TYPE: DNA
<213> ORGANISM: Artificial Sequence
<220> FEATURE:
<223> OTHER INFORMATION: antisense primer - RSVf-R

<400> SEQUENCE: 8
gatcctgcat trtcacarta cca                                              23

<210> SEQ ID NO 9
<211> LENGTH: 18
<212> TYPE: DNA
<213> ORGANISM: Artificial Sequence
<220> FEATURE:
<223> OTHER INFORMATION: MGB probe - RSVfA

<400> SEQUENCE: 9
tgtagtacaa ttrccact                                                    18

<210> SEQ ID NO 10
<211> LENGTH: 255
```

```
<212> TYPE: DNA
<213> ORGANISM: Artificial Sequence
<220> FEATURE:
<223> OTHER INFORMATION: standard DNA

<400> SEQUENCE: 10
tgtccaacaa tgttcaaata gttagacagc aaagttactc tatcatgtcc ataataaaag      60
aggaagtctt agcatatgta gtacaattac cactatatgg tgttatagat acaccctgtt     120
ggaaactaca cacatcccct ctatgtacaa ccaacacaaa agaagggtcc aacatctgtt     180
taacaagaac tgacagagga tggtactgtg acaatgcagg atcagtatct ttcttcccac     240
aagctgaaac atgta                                                      255

<210> SEQ ID NO 11
<211> LENGTH: 42
<212> TYPE: PRT
<213> ORGANISM: respiratory syncytial virus

<400> SEQUENCE: 11

Lys Pro Lys Asp Asp Tyr His Phe Glu Val Phe Asn Phe Val Pro Cys
1               5                   10                  15

Ser Ile Cys Gly Asn Asn Gln Leu Cys Lys Ser Ile Cys Lys Thr Ile
            20                  25                  30

Pro Ser Asn Lys Pro Lys Lys Lys Pro Thr
        35                  40
```

RSV F/G CHIMERIC VACCINE

The present invention relates to a vaccine of respiratory syncytial virus (RSV). More specifically, the present invention relates to a recombinant F/G chimeric protein obtained by using RSV F protein as a basic structure, and substituting a portion of the basic structure with a whole or a portion of a Conserved Central Domain sequence of RSV G protein, or adding a whole or a portion of the Conserved Central Domain sequence to the basic structure.

BACKGROUND ART

Epidemiology:

Infection route of RSV is droplet infection or contact infection, and nearly 100% of a human are infected by the age of two. Usually, cold-like symptoms such as runny nose, fever of 38 to 39° C., and cough appear. On the other hand, primary infection often progresses to bronchiolitis and pneumonia, and in particular, infants under six months and elderly people are likely to be severe. According to global estimation in 2015, 33.1 million people under the age of five suffer from RSV infection (RSV-Acute Lower Respiratory Infection), of which 3.2 million people require hospitalization and 118,200 people die (Non-Patent Document 1). A method of treatment is mainly supportive care, and inhalation of an antiviral agent Ribavirin (VIRAZOLE (registered trademark)) is only approved in the United States as a therapeutic agent. The antibody drug, Palivizumab (Synagis (registered trademark)), that binds to an envelope protein of RSV is approved as only a preventive agent, but the administration subject is limited to a high risk person (premature baby, chronic disease, congenital heart disease, etc.) (Non-Patent Document 7). It is said that a child having RS virus infection, particularly bronchiolitis, in infancy is likely to develop bronchial asthma later in life. However, since it is not possible to prevent infection, effective vaccine development has been expected for many years, but there is no RSV vaccine approved worldwide.

RSV F Protein:

RSV F protein is localized on the RSV envelope surface and has an important function for a virus to enter a host cell. Specifically, infection is established by fusing a host cell membrane and a viral envelope via RSV F protein. Since there are few mutations between virus strains, research and development using RSV F protein as a vaccine antigen has progressed. So far, RSV F protein has been reported to take three forms (Prefusogenic F/Prefusion F/Postfusion F) (Patent Documents 1, 4, and 5). Therefore, research and development using each form of RSV F protein as a vaccine antigen have been conducted, and a plurality of clinical trials have been conducted (Non-Patent Document 2). RSV F protein is about 60 kDa, and has a basic structure generally composed of sites called a Signal Peptide (SP) domain, a Fragment 2 (F2) domain, a p27 domain, a Fusion Peptide (FP) domain, a Fragment 1 (F1) domain, a Transmembrane (TM) domain, and a Cytoplasmic tail (CT) domain, in order from the N-terminus.

RSV G Protein:

RSV G protein is localized on the RSV envelope surface and has an important function for a virus to adhere to a host cell. Specifically, the virus adheres to a receptor of host cell via RSV G protein on the viral surface. The sequence of RSV G protein varies greatly between virus strains, and is roughly divided into subgroups A and B depending on the difference in sequence. The G protein of RSV A2 strain is about 30 kDa, and is composed of sites called Intravirion, transmembrane region (TM), Mucin-like region I, Conserved Central Domain (CCD), and Mucin-like region II, in order from the N-terminus. A region sequence (amino acid residues 158 to 199) called CCD is less variable between virus strains and highly conserved, and comprises chemokine CX3C motif. The CX3C motif binds to CX3C Receptor 1 (CX3CR1) on a cell surface serving as a ligand, and the virus and the cell adhere to each other, thereby promoting infection (Non-Patent Document 3). The RSV F protein then promotes fusion of the viral envelope with the cell membrane to establish infection. Since the RSV G protein is also important for infection together with the RSV F protein, research and development using the RSV G protein as a vaccine antigen have been conducted, and clinical trials have been performed (Patent Document 3).

RSV F/G Chimeric Protein:

As RSV F/G chimeric proteins, there is published information of a chimeric respiratory syncytial virus (RSV) polypeptide comprising (i) a first F protein polypeptide domain, (ii) a polypeptide domain of G protein, and (iii) a second F protein polypeptide, in the N-terminal to C-terminal direction (Patent Document 6). The G protein contained in the chimeric antigen is any of amino acid residues 183 to 203, 152 to 229, 149 to 229, and 128 to 229 (Patent Document 6). There is also public information of a chimeric RSV polypeptide comprising (i) an amino acid sequence in which first F protein and second F protein are linked so as not to be cleaved at a Furin cleavage site, and (ii) a portion of a G protein polypeptide, in the N-terminal to C-terminal direction (Patent Document 7). The G protein contained in the chimeric antigen is any of amino acid residues 183 to 203, 152 to 229, and 149 to 229 (Patent Document 7). Although all of them are RSV F/G chimeric proteins, evaluation of superiority and equivalence of infection protective ability with RSV wild type F (RSV WT F) protein, RSV Postfusion F (RSV post F) protein, and RSV pre F (RSV Prefusion F) protein, and enhancement of infection by low dose administration have not been verified. Difference of the present invention lies in that the G protein contained in the chimeric antigen is limited to a CCD region. That is, the present invention is limited to a region important for efficacy and safety: amino acid residues 158 to 199.

As RSV F/G chimeric protein, there is a report of a protein in which amino acid residues 1 to 526 of RSV F protein and amino acid residues 69 to 298 of RSV G protein are linked in the N-terminal to C-terminal direction (Non-Patent Document 5). The RSV F/G chimeric protein has superiority in evaluation of infection protective ability and evaluation of side effects in comparison with formalin-inactivated RSV. However, in comparison with RSV WT F protein, RSV post F protein and RSV pre F protein, evaluation of superiority and equivalence in the infection protective ability and enhancement of infection by low dose administration have not been verified (Non-Patent Document 5). Although basic researches have been conducted on the RSV F/G chimeric proteins, no clinical studies have been conducted yet. Difference of the present invention lies in that the G protein contained in the chimeric antigen is limited to a CCD region. That is, the present invention is limited to a region important for efficacy and safety: amino acid residues 158 to 199.

Anti-RSV F Antibody:

An RSV F protein-specific antibody is known to have neutralizing function. Monoclonal antibodies are each present in multiple epitopes of RSV F protein (Non-Patent Document 6). One of antibodies specific to a site called siteII of RSV F protein is approved as an antibody drug, Palivizumab (Synagis (registered trademark)). This drug is also approved as a preventive agent, but the administration subject is limited to a high risk person (premature baby, chronic disease, congenital heart disease, etc.) (Non-Patent Document 7).

Anti-RSV G Antibody:

An RSV G protein-specific antibody has neutralizing function similar to the anti-RSV F antibody. In particular, a plurality of antibodies against CCD of RSV G protein are known (Non-Patent Document 4). Among them, an antibody called 3D3 has been reported to have an effect of not causing exacerbation of symptoms such as airway inflammation due to infection, unlike palivizumab, in a BALB/c mouse model (Patent Document 2, Non-Patent Documents and 9). In addition, it has been reported that an antibody called 131-2G had an effect of inducing a shift from T helper (Th) 2 to Th1 in RSV infection in BALB/c mice (Non-Patent Document 10).

Among the sequences of CCD of RSV G protein that are highly conserved among virus strains, there exists a particularly highly conserved sequence region, Central Conserved Region (CCR), which is located at amino acid residues 164 to 176 of RSV G protein (Non-Patent Documents 11 and 19). 3D3, 131-2G and 2B11, which are monoclonal antibodies recognizing the CCR, have been reported to have an effect of suppressing lung inflammation in a BALB/c mouse model (Non-Patent Document 11).

Exacerbation Mechanism of RSV Infection:

Formalin-inactivated RSV vaccine trial was conducted in the 1960's, but the hospitalization rate in RSV primary infection was 2% in a non-vaccinated group and 80% in a vaccinated group, and two children died in the vaccinated group (Non-Patent Document 12). As causes of symptom exacerbation by RSV infection after vaccination, induction of immunity to Th2 by RSV G protein, induction of immunity to Th2 by carbonylated protein produced by formalin treatment, low avidity of antibodies induced by vaccine and the like have been mentioned (Non-Patent Documents 13 to 15).

Relationship Between RSV G Protein and Exacerbation Mechanism:

It is known that infants become severe particularly with RSV infection. As one of the causes, it has been mentioned that immunity of infants is shifted to Th2 in which many inflammatory cells are present. In addition, it has been reported in a human with RSV infection that when RSV is infected with neonatal regulatory B lymphocytes (nBreg) via CX3CR1 which is a receptor of CX3C motif of RSV G protein, IL-10 is produced and Th1 response is inhibited (Non-Patent Document 16).

Symptom Exacerbation by Low Dose Administration:

There is a report that Vaccine-Enhanced Disease such as alveolitis occurred in a cotton rat model when the rat was administered at low dose with a prior developing product, a vaccine comprising RSV post F protein (comprising Th1-induced Glucopyranosyl Lipid Adjuvant-stable Emulsion as an adjuvant) and RSV pre F protein (comprising Th2-induced Aluminium hydroxide hydrate Gel as an adjuvant) as antigens, and then infected with RSV (Non-Patent Document 17).

PRIOR ART

Patent Document

Patent Document 1: Japan patent 6162751
Patent Document 2: Japan patent 5808536
Patent Document 3: Japan patent 4310184
Patent Document 4: WO2016144675A1
Patent Document 5: JP 2016-519658
Patent Document 6: JP 2010-522540
Patent Document 7: JP 2011-528222
Patent Document 8: Japan patent 4150814

Non-Patent Document

Non-Patent Document 1: Shi T et al. Lancet. 2017 Sep. 2; 390(10098):946-958.
Non-Patent Document 2: Mazur N I et al. Lancet Infect Dis. 2018 October; 18(10):e295-e311.
Non-Patent Document 3: Johnson S M et al. PLoS Pathog. 2015 Dec. 11; 11(12):e1005318
Non-Patent Document 4: Fedechkin S O et al. Sci Immunol. 2018 Mar. 9; 3(21). pii: eaar3534.
Non-Patent Document 5: Prince G A et al. J Virol. 2000 November; 74(22):10287-92.
Non-Patent Document 6: McLellan J S et al. Science. 2013 May 31; 340(6136):1113-7.
Non-Patent Document 7: Anti-RS virus humanized monoclonal antibody preparation: Synagis® Solution for Intramuscular Administration; attached document
Non-Patent Document 8: Han J et al. Am J Respir Cell Mol Biol. 2014 July; 51(1):143-54.
Non-Patent Document 9: http://www.trellisbio.com/pipeline/viruses.html
Non-Patent Document 10: Boyoglu-Barnum S et al. J Virol. 2014 September; 88(18):10569-83.
Non-Patent Document 11: Caidi H et al. Antiviral Res. 2018 June; 154:149-157
Non-Patent Document 12: Kim H W et al. Am J Epidemiol. 1969 April; 89(4):422-34.
Non-Patent Document 13: Johnson T R et al. Pediatr Infect Dis J. 2004 January; 23(1 Suppl):S46-57
Non-Patent Document 14: Moghaddam A et al. Nat Med. 2006 August; 12(8):905-7.
Non-Patent Document 15: Delgado M F et al. Nat Med. 2009 January; 15(1):34-41.
Non-Patent Document 16: Zhivaki D et al. Immunity. 2017 Feb. 21; 46(2):301-314.
Non-Patent Document 17: Schneider-Ohrum K et al. J Virol. 2017 Mar. 29; 91(8). pii: e02180-16.
Non-Patent Document 18: N Elango et al. Nucleic Acids Res. 1985 Mar. 11; 13(5): 1559-1574.
Non-Patent Document 19: Sullender W et al. Virology. 1995 May 10; 209(1):70-9.
Non-Patent Document 20: Yokoi H et al. Kansenshogaku Zasshi. 2012 September; 86(5):569-76.
Non-Patent Document 21: Wu S J et al. J Gen Virol. 2007 October; 88(Pt 10):2719-23.
Non-Patent Document 22: McLellan J S et al. J Virol. 2010 December; 84(23):12236-44.
Non-Patent Document 23: Gilman M S et al. Sci Immunol. 2016 Dec. 16; 1(6).
Non-Patent Document 24: Tang A et al. Nat Commun. 2019 Sep. 12; 10(1):4153.

DISCLOSURE OF THE INVENTION

Technical Problem to be Solved by the Invention

By the age of two, nearly 100% of a human are infected with RSV, and cold-like symptoms usually appear. On the other hand, primary infection often progresses to bronchiolitis and pneumonia, and in particular, infants and elderly people are likely to be severe. There is Palivizumab (Synagis (registered trademark)) as a preventive agent, but the administration subject is limited to a high risk person (premature baby, chronic disease, congenital heart disease, etc.). There are only a number of RSV vaccines in clinical trial stage, and there is still no approved RSV vaccine worldwide. Since exacerbating responses were observed in natural infection after formalin-inactivated RSV vaccination in clinical trials in the 1960's, development of an RSV vaccine that can avoid risk of exacerbation has been required. In particular, while there is a concern about exacerbating responses in infants, the development of the RSV vaccine capable of avoiding this risk has not progressed. Under such circumstances, it is an object of the present invention to provide an RSV vaccine that can avoid risk of exacerbation after vaccination.

Means for Solving the Problems

The present inventors have surprisingly found that an RSV F/G chimeric protein antigen prepared by using RSV F protein as a basic structure, and substituting a portion of the basic structure with a whole or a portion of a CCD sequence of RSV G protein, or adding a whole or a portion of the CCD sequence to the basic structure hardly causes an enhancement of infection observed when infected with RSV after low dose inoculation of a post F protein antigen and a pre F protein antigen. Also, the present inventors have proved that infection protective ability is superior to that of the post F protein antigen, and the infection protective ability is equivalent to that of the pre F protein antigen. In addition, the present inventors have found that expression levels of RSV F protein, RSV F protein comprising a mutated amino acid sequence, and F/G chimeric protein are improved by adding modification of glycosylation to the RSV F protein.

In the prior developing product using the post F protein and the pre F protein as vaccine antigens, an anti-RSV F antibody to be induced has infection protective ability. However, it is presumed that when blood concentration of the anti-RSV F antibody decreases, neutralizing capacity decreases, and a so-called antibody-dependent enhancement of infection in which infection is promoted via cells capturing the anti-RSV F antibody simultaneously occurs, which results in causing VED.

On the other hand, it can be expected that an anti-RSV G antibody is induced in addition to the anti-RSV F antibody by administering the RSV F/G chimeric protein antigen. A feature of the present invention different from the RSV F/G chimeric protein reported in the past is that G protein to be contained in a chimeric antigen is limited to a CCD region (amino acid residues 158 to 199) that is important for efficacy and safety. Therefore, the anti-RSV G antibody to be induced by immunizing the RSV F/G chimeric protein has infection protective ability similar to the anti-RSV F antibody. In addition, since the RSV F/G chimeric protein incorporates sequences around CX3C motif derived from the G protein, the immune-induced anti-RSV G antibody binds to the vicinity of the CX3C motif of the G protein localized on the viral surface. As a result, the CX3C motif of the viral surface G protein is masked with the anti-RSV G antibody, and it is presumed that binding to CX3CR1 localized on a host cell surface is inhibited. Therefore, it is expected to suppress Th1 response inhibition signal via CX3C-CX3CR1. That is, it is suggested that normal Th1 response is promoted by the anti-RSV G antibody to be induced by immunizing the RSV F/G chimeric protein antigen, which results in the suppression of infection enhancement.

In addition, when mice were immunized with a pre F protein antigen and an RSV F/G chimeric protein antigen, subclass analysis of anti-RSV F antibodies induced in blood was performed. As a result, the amount of IgG2a with complement-binding ability tended to increase in the mice immunized with the RSV F/G chimeric protein antigen as compared with in the mice immunized with the pre F protein antigen. Therefore, the RSV F/G chimeric protein antigen can be expected to have a more effective infection protective effect by a complement system as compared with the pre F protein antigen.

As in the mechanism described above, by administering the RSV F/G chimeric protein antigen found by the inventors, an effect of improving infection protective ability and/or an effect of preventing infection enhancement can be expected as compared with vaccine administration using only the RSV F protein as an antigen.

The present invention provides the following [1] to [25].

[1] A chimeric protein (RSV F/G protein) of Respiratory Syncytial Virus (RSV) F protein and G protein wherein a portion of RSV F protein as a basic structure is replaced with a whole or a portion of CCD sequence of RSV G protein or wherein a whole or a portion of CCD sequence of RSV G is added to the basic structure.

[2] The chimeric protein of [1] wherein an amino acid sequence of the F protein comprises a sequence having a homology of 90% or more to the amino acid sequence of SEQ ID NO: 1.

[3] The chimeric protein of [1] wherein an amino acid sequence of the F protein comprises the amino acid sequence of SEQ ID NO: 1.

[4] The chimeric protein of any one of [1] to [3] wherein the replacement with a whole or a portion of the CCD sequence or the addition of a whole or a portion of the CCD sequence occurs at FP domain of the F protein.

[5] The chimeric protein of any one of [1] to [3] wherein the replacement with a whole or a portion of the CCD sequence occurs at FP domain and p27 domain of the F protein.

[6] The chimeric protein of [5] wherein the replacement with a whole or a portion of the CCD sequence occurs at positions 137 to 146 of the F protein.

[7] The chimeric protein of any one of [1] to [3] wherein the replacement with a whole or a portion of the CCD sequence or the addition of a whole or a portion of the CCD sequence occurs at F1 domain of the F protein.

[8] The chimeric protein of [7] wherein the replacement with a whole or a portion of the CCD sequence occurs at positions 382 to 393 or at positions 425 to 436 of the F protein.

[9] The chimeric protein of [2] or [3] wherein the addition of a whole or a portion of the CCD sequence occurs at the C-terminal of the F protein.

[10] The chimeric protein of any one of [1] to [9] wherein an amino acid sequence of a whole or a portion of the CCD sequence comprises a sequence selected from the group consisting of the sequences at positions 158 to 199, 162 to 197, 164 to 190, 164 to 186, 164 to 176, 173 to 197, 187 to 197, 173 to 186, and 162 to 171 of SEQ ID NO: 2, a sequence consisting of the sequences at positions 162 to 172 and 187 to 199 of SEQ ID NO: 2 linked to each other, a sequence consisting of the sequences at positions 164 to 172 and 187 to 197 of SEQ ID NO: 2 linked to each other, a sequence consisting of the sequences at positions 162 to 172, 187 to 199 and 162 to 172 of SEQ ID NO: 2 linked to each other, and a sequence consisting of two or three of the sequences at position 162 to 172 of SEQ ID NO: 2 linked to each other.

[11] The chimeric protein of [10] wherein the linkage of amino sequences is done using a linker.

[12] The chimeric protein of any one of [1] to [11] wherein the replacement with a whole or a portion of the CCD sequence or the addition of a whole or a portion of the CCD sequence is done using a linker.

[13] The chimeric protein of [11] or [12] wherein an amino acid sequence of the linker is GGGGS (SEQ ID NO: 5) or EAAAK (SEQ ID NO: 6).

[14] The chimeric protein of any one of [10] to [13] wherein an amino acid sequence of a whole or a portion of the CCD sequence has a homology of 75% or more to said amino acid sequence.

[15] The chimeric protein of any one of [10] to [13] wherein an amino acid sequence of a whole or a portion of the CCD sequence has a homology of 90% or more to said amino acid sequence.

[16] The chimeric protein of any one of [1] to [15] wherein a glycosylation site is introduced into the F protein by amino acid modification.

[17] The chimeric protein of [16] wherein the glycosylation site is introduced into the vicinity of siteIV of the F protein, i.e. at positions 419 to 468 of SEQ ID NO: 1.

[18] The chimeric protein of [17] wherein the glycosylation site of siteIV is at any of positions 419 to 468 of SEQ ID NO: 1.

[19] The chimeric protein of [18] wherein an amino acid modification for introduction of the glycosylation site of siteIV is any one of the following (1) to (7):

(1) G430T/S
(2) K419N and K421T/S
(3) K427N and R429T/S
(4) T434N and S436T/S
(5) K419N, K421T/S, and G430T/S
(6) K419N, K421T/S, and K427N and R429T/S
(7) K419N, K421T/S, and T434N and S436T/S.

[20] The chimeric protein of any one of [16] to [19] wherein glycosylation occurs at a glycosylation site.

[21] An RSV vaccine comprising as an antigen the chimeric protein of any one of [1] to [20].

[22] The RSV vaccine of [21] wherein the vaccine has a lower exacerbation tendency of RSV infection than RSV F protein.

[23] A method for improving an expression level of RSV F protein which comprises introducing a glycosylation site into the F protein by amino acid modification thereof and allowing glycosylation to occur.

[24] The method of [23] wherein a portion of the F protein is replaced with a whole or a portion of CCD sequence of RSV G protein or wherein a whole or a portion of the CCD sequence is added to the CCD sequence of RSV G protein.

[25] The method of [23] or [24] wherein an amino acid modification for introduction of the glycosylation site is any one of the following (1) to (7):

(1) G430T/S
(2) K419N and K421T/S
(3) K427N and R429T/S
(4) T434N and S436T/S
(5) K419N, K421T/S and G430T/S
(6) K419N, K421T/S and K427N and R429T/S
(7) K419N, K421T/S and T434N and S436T/S.

Effect of the Invention

According to the present invention, it is possible to provide a vaccine having an effect of preventing RSV infection and/or a vaccine capable of avoiding exacerbation of RSV infection after vaccination, and further a vaccine having an effect of preventing RSV infection and capable of avoiding exacerbation of RSV infection after vaccination.

BRIEF DESCRIPTION OF DRAWINGS

FIG. 2 shows schematic diagrams of RSV G protein sequences to be a portion of the RSV F/G chimeric protein. Row Nos 1 to 9 depict portions of the CCD sequence of the RSV G protein comprising residues 158 to 199 of SEQ ID NO:1.

FIG. 4 shows schematic diagrams of RSV G protein sequences to be a portion of the RSV F/G chimeric protein. Row Nos 15 to 18 depict portions of the CCD sequence of the RSV G protein comprising residues 158 to 199 of SEQ ID NO: 1 in conjunction with linkers GGGGS (SEQ ID NO: 5) and/or EAAAK (SEQ ID NO: 6).

FIG. 5 is a list of expression levels of RSV F/G chimeric proteins.

FIG. 6 is a list of expression levels of RSV F/G chimeric proteins.

FIG. 10 shows the results of SDS-PAGE of RSV F/G chimeric proteins.

FIG. 11 shows the results of SDS-PAGE of RSV F/G chimeric proteins.

FIG. 16 shows electron microscopic images of RSV F/G chimeric proteins.

FIG. 17 shows the results of ELISA test of RSV F/G chimeric proteins.

FIG. 18 shows the results of ELISA test of RSV F/G chimeric proteins.

FIG. 28 shows the results of SDS-PAGE of RSV F/G chimeric proteins.

FIG. 29 shows the results of SDS-PAGE of RSV F/G chimeric proteins.

FIG. 34 shows the results of SDS-PAGE of RSV F/G chimeric proteins.

FIG. 35 shows the results of SDS-PAGE of RSV F/G chimeric proteins.

Figures 36, 37:
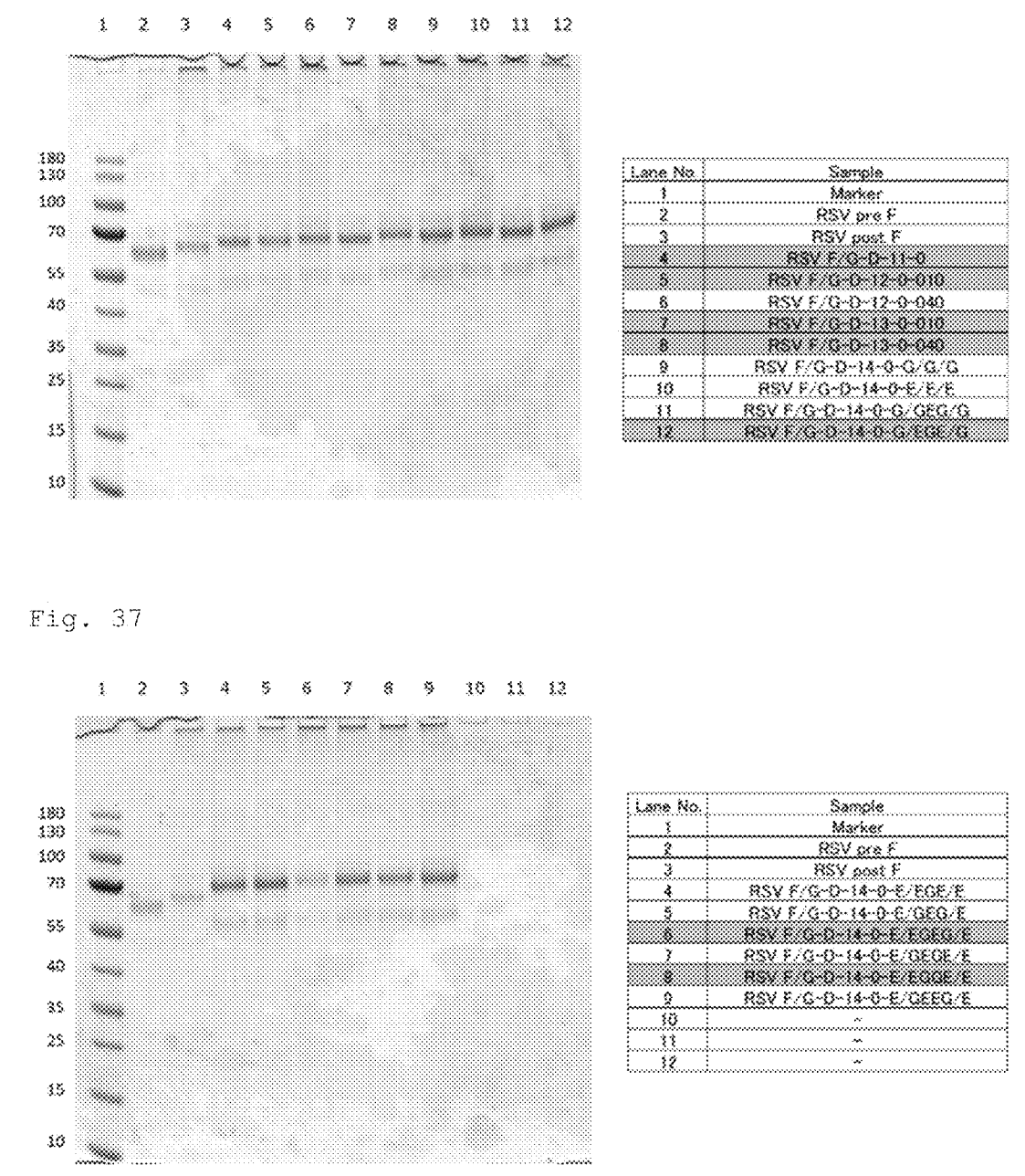

FIG. 36 shows the results of SDS-PAGE of RSV F/G chimeric proteins.

FIG. 37 shows the results of SDS-PAGE of RSV F/G chimeric proteins.

FIG. 40 shows the results of ELISA test of RSV F/G chimeric proteins.

FIG. 41 shows the results of ELISA test of RSV F/G chimeric proteins.

FIG. 42 shows the results of complement-dependent neutralization test of RSV F/G chimeric protein immune sera.

BEST MODE FOR CARRYING OUT THE INVENTION

Definitions

As used herein, the term "enhancement of infection" refers to an increase in infectivity titer or viral copy number when an antigen is immunized and then infected with RSV as compared with a control group infected with RSV without immunizing the antigen.

Figure 1:
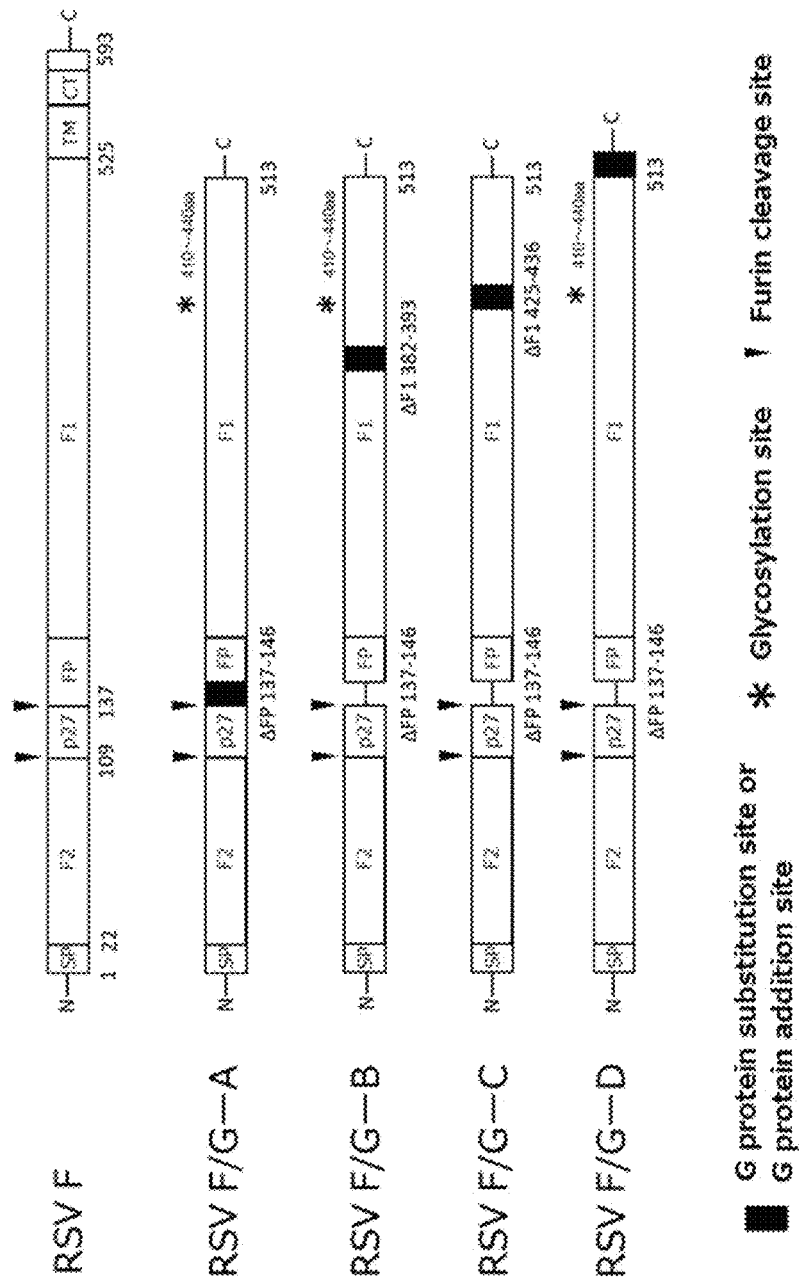
FIG. 1 shows schematic diagrams of RSV F/G chimeric protein sequences.
Figure 2:
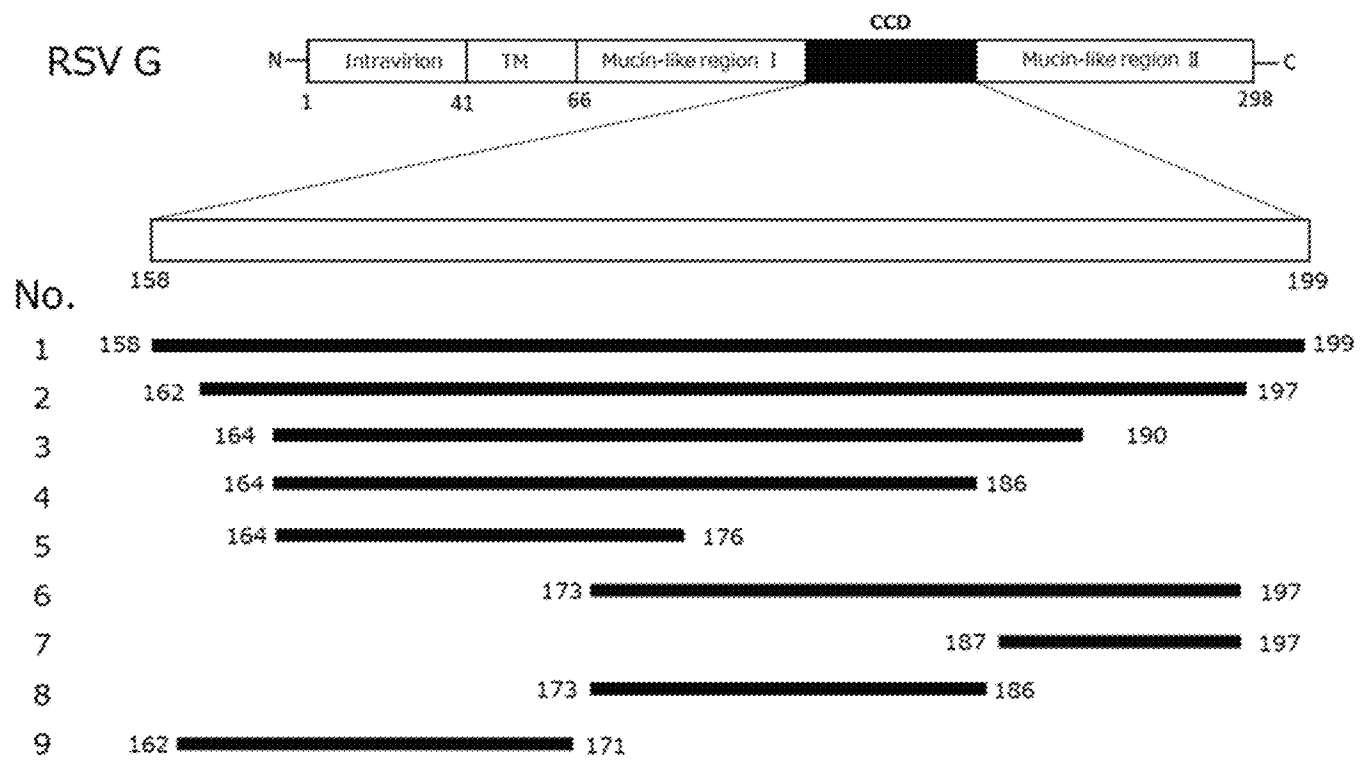
Figure 3:
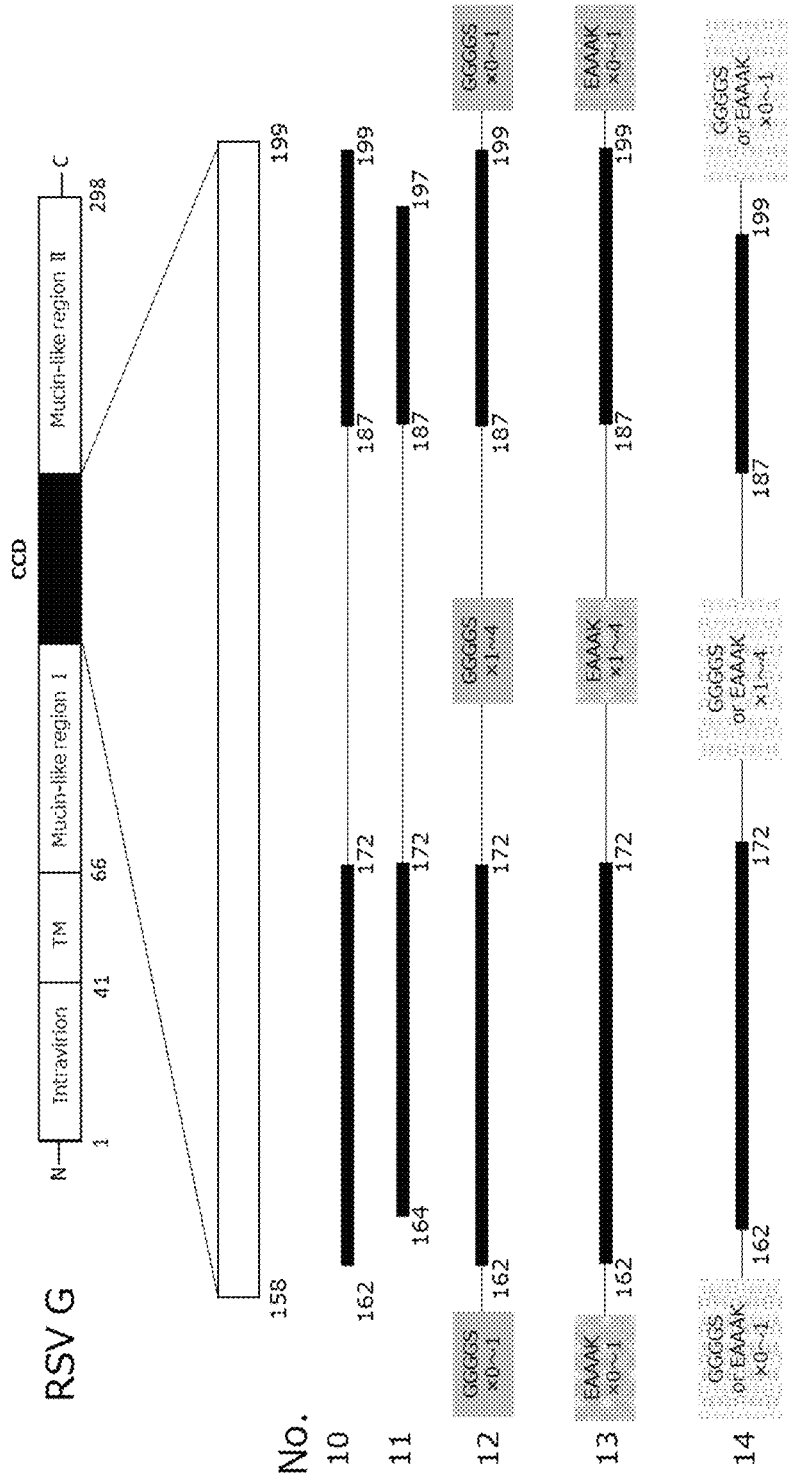
FIG. 3 shows schematic diagrams of RSV G protein sequences to be a portion of the RSV F/G chimeric protein. Row Nos 10 to 14 depict portions of the CCD sequence of the RSV G protein comprising residues 158 to 199 of SEQ ID NO:1 in conjunction with linkers GGGGS (SEQ ID NO: 5) and/or EAAAK (SEQ ID NO: 6).
Figure 4:
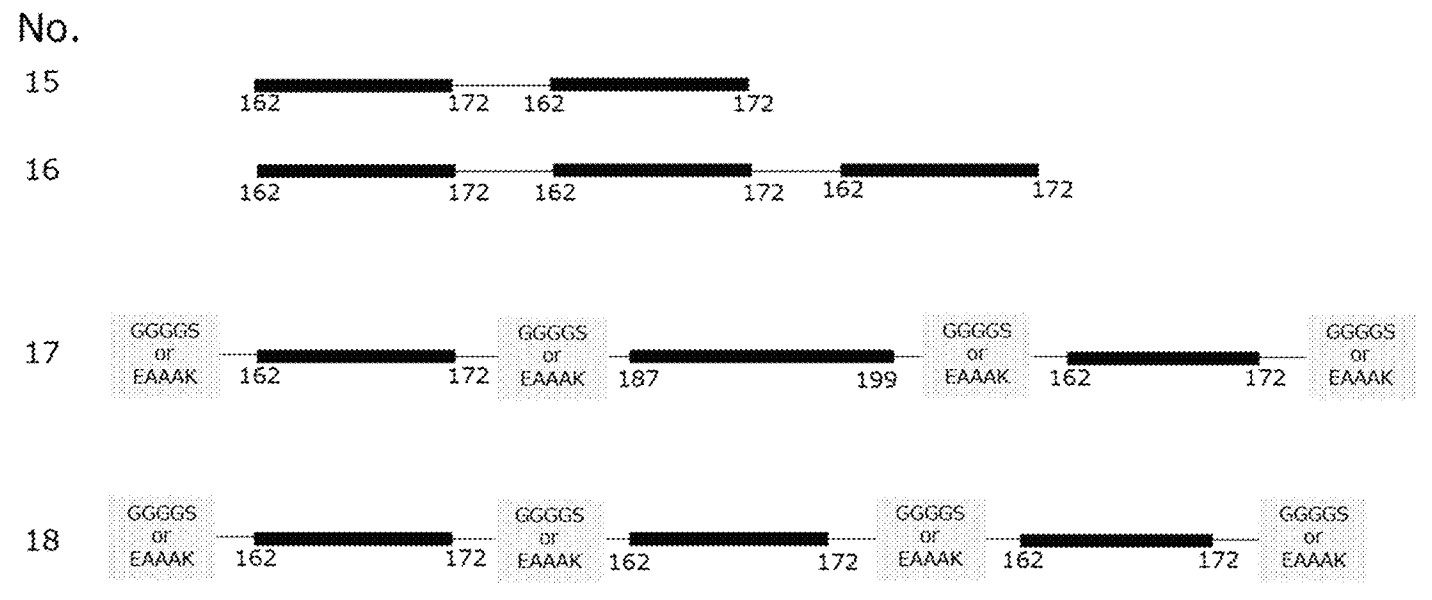

As used herein, the term "RSV F/G-W-X-Y Z" is a name based on characteristics of RSV F/G chimeric protein. "W" represents a substitution position with G protein or an addition position of G protein in RSV F protein (basic structure) by alphabets A to D (FIG. 1). In the case of two letters of the alphabet, it means that there are substitutions with G protein or additions of G protein at two positions. For example, the case of "AD" means that there are substitutions or additions at positions of A and D. "X" represents an RSV G protein sequence substituting the basic structure or added to the basic structure with the number of 1 to 18 (FIGS. 2 to 4). When there are two numbers, it means that there are substitutions or additions in two corresponding G protein sequences. For example, the case of "RSV F/G-AD-9/7" means that there are substitutions with, or additions of, "9 at position A" and "7 at position D". When there is no substitution with G protein or addition of G protein, it is represented by 0. "Y" represents amino acid modification of RSV F protein accompanied by a sugar chain modification, by the number 0 to 4, and specifically means "0: no modification, 1: K419N, K421T and G430T, 2: K419N, K421T, T434N and S436T, 3: K421N and G430T, 4: K419N, K421T, K427N, and R429T". Here, for example, the notation "K419N" indicates that lysine (K) at position 419 of the RSV F protein is substituted with asparagine (N). Also, for example, the notation "K421T/S" indicates that lysine (K) at position 421 is substituted with threonine (T) or serine(S). Note that "Z" represents other modifications or the number and type of linkers. Specifically, as other modifications, one obtained by deleting 136 amino acids of RSV F protein is denoted by A136aa, and one obtained by substituting arginine at position 136 with glutamine is denoted by R136Q. The number of linkers is shown as "0:0, 1:1, 2:2, 3:3, 4:4", and the number of linkers is shown in order from the left side of three linker insertion positions of Nos. 12 and 13 in FIG. 3. For example, when the numbers of linkers are 0, 4, and 0, it is indicated as "040". In addition, the type of linker is shown as "GGGGS linker: G, EAAAK linker: E", where GGGGS is SEQ ID NO: 5 and EAAAK is SEQ ID NO: 6, and is shown in order from the left side of three or four linker insertion positions of No. 14 in FIG. 3 and Nos. 17 and 18 in FIG. 4, and a separator between the linker and the G protein sequence is represented using "/" to show the type of linker. Then, when there is an amino acid mutation at the end of the name, for example, the notation "N191S", it indicates that N at position 191 of SEQ ID NO: 1 is substituted with S. Moreover, "Seq11" at the end of the name indicates a G protein sequence of SEQ ID NO: 11.

Hereinafter, preferred embodiments of the present invention will be described in detail. However, the present invention is not limited to the following embodiments.

(RSV F/G Chimeric Vaccine)

The vaccine (RSV F/G chimeric vaccine) according to the present embodiment is a formulation using a recombinant RSV F/G chimeric protein obtained by using RSV F protein as a basic structure, and substituting a portion of the basic structure with a whole or a portion of a CCD sequence of RSV G protein, or adding a whole or a portion of the CCD sequence to the basic structure, as an antigen. Here, "adding" includes the meaning of "inserting", and "substituting" or "adding" may be via a linker with the basic structure. An example of the amino acid sequence of the linker includes GGGGS (SEQ ID NO: 5) or EAAAK (SEQ ID NO: 6).

Examples of a substitution position with the G protein or an addition position of the G protein in the RSV F protein (basic structure) include an FP domain of the F protein, an FP domain and a p27 domain of the F protein (RSV F/G-A in FIG. 1), specifically, positions 137 to 146 of the F protein, an F1 domain of the F protein, specifically, positions 382 to 393 (RSV F/G-B in FIG. 1) or positions 425 to 436 of the F protein (RSV F/G-C in FIG. 1), and the C-terminus of the F protein (RSV F/G-D in FIG. 1). In addition, the substitution position with the G protein or the addition position of the G protein in the RSV F protein (basic structure) may be a position away from a known epitope on the three-dimensional structure of the protein, and examples thereof include RSV F/G-A, RSV F/G-D, and the like. Alternatively, it may be a conspicuous position (known epitope or the like) as a protein antigen, for example, RSV F/G-B (position of antigenic siteI), RSV F/G-C (position of antigenic siteIV), or the like. The substitutions of RSV F/G-B and RSV F/G-C may be a whole or a portion of amino acid residues 382 to 393 and 425 to 436 shown in FIG. 1.

The RSV F/G chimeric vaccine has excellent infection protective ability as compared with that of a vaccine using the post F protein as an antigen, and has infection protective ability equal to or higher than that of a vaccine using the pre F protein as an antigen. Surprisingly, the RSV F/G chimeric protein vaccine suppresses enhancement of RSV infection after vaccination, as compared with a vaccine using the post F protein and the pre F protein as antigens.

Examples of sequences of the RSV F protein used as the basic structure include sequences derived from known wild-type RSV strains or clinical isolates. For example, the sequence may be a sequence registered in databases of GenBank, European Bioinformatics Institute (EBI), and DNA Data Bank of Japan (DDBJ). Examples of representative sequences of the RSV F protein include a sequence set forth in SEQ ID NO: 1. The RSV F protein is generally composed of sites called an SP domain, an F2 domain, a p27 domain, an FP domain, an F1 domain, a TM domain, and a CT domain, in order from the N-terminus.

Examples of sequences of the RSV G protein to be a portion of the RSV F/G chimeric protein include sequences derived from known wild-type RSV strains or clinical isolates. For example, the sequence may be a sequence registered in databases of GenBank, European Bioinformatics Institute (EBI), and DNA Data Bank of Japan (DDBJ). Examples of representative sequences of the RSV G protein include a sequence set forth in SEQ ID NO: 2 (Human respiratory syncytial virus A2, UniProtKB/Swiss-Prot: Accession No. P03423). In addition, as a representative sequence of G-protein CCD of an RSV B strain, there are a sequence set forth in SEQ ID NO: 11 (Human respiratory syncytial virus B (strain B1), UniProtKB/Swiss-Prot: Accession No. O36633), and the like.

The RSV F/G chimeric protein according to the present invention is prepared by substituting a portion of the RSV F protein with a whole or a portion of the CCD sequence of the RSV G protein, or adding a whole or a portion of the CCD sequence to the RSV F protein. Here, a whole or a portion of the CCD sequence of the RSV G protein substituted or added may be a sequence derived from a region including a central conserved region (CCR) (amino acid residues 164 to 176 of the RSV G protein) that are sequence regions particularly highly conserved in a sequence of CCD of the RSV G protein (amino acid residues 158 to 199 of the RSV G protein) highly conserved among RSV strains, or a CX3C motif (amino acid residues 182 to 186 of the RSV G protein), for example, a sequence derived from amino acid residues 158 to 199 of the RSV G protein. More specifically, in the present invention, a whole or a portion of the CCD sequence may include, for example, a sequence at positions 158 to 199 of SEQ ID NO: 2, a sequence at positions 162 to 197, a sequence at positions 164 to 190, a sequence at positions 164 to 186, a sequence at positions 164 to 176, a sequence at positions 173 to 197, a sequence at positions 187 to 197, a sequence at positions 173 to 186, a sequence at positions 162 to 171, one in which a sequence at positions 162 to 172 and a sequence at positions 187 to 199 are linked, one in which a sequence at positions 164 to 172 and a sequence at positions 187 to 197 are linked, or one in which two to three sequences at positions 162 to 172 are linked (FIGS. 2 to 4). In the present invention, a whole or a portion of the CCD sequence may have a homology of 75% or more, preferably 85% or more, and more preferably 90% or more with a sequence comprising each of the sequences. The sequence of the F protein may be different from that of SEQ ID NO: 1 by about 90% depending on a known wild-type strain. In addition, although the CCD sequence of the G protein is conserved among virus strains, a portion of the CCD sequence excluding the CCR sequence may be different between known wild strains and clinical isolates by about 75% as compared with SEQ ID NO: 2. In addition, the RSV F protein is generally composed of sites called an SP domain, an F2 domain, a p27 domain, an FP domain, an F1 domain, a TM domain, and a CT domain, in order from the N-terminus, but the TM and CT domains on the C-terminal side are regions that do not go out of the cell, and thus may not comprise these domains.

The RSV F/G chimeric protein according to the present invention can also improve expression level by modifying glycosylation of the RSV F protein. The modification of glycosylation may be one in which an N-type sugar chain is added to an amino acid residue N (Asn) and an O-type sugar chain is added to an amino acid residue T (Thr)/S (Ser). Modification (mutation) can be added to the RSV F protein for the modification of glycosylation, and the amino acid sequence after modification may comprise an amino acid sequence motif of N (Asn)-α (amino acid other than Pro)-T (Thr) or N (Asn)-α (amino acid other than Pro)-S (Ser).

The position where a modification (mutation) is added to the RSV F protein for modification of glycosylation is preferably around positions 422 to 468 (Non-Patent Documents 21, 22, and 24) of the RSV F protein called siteIV span to which monoclonal antibody 101F or the like to the RSV F protein specifically binds, that is, positions 419 to 468 of the RSV F protein, and a more preferable position is an amino acid residue at any of positions 419 to 436 of the RSV F protein. Specifically, it is preferable to add modification (mutation) to any of the following amino acid residues (1) to (7).

(1) G430T/S
(2) K419N and K421T/S
(3) K427N and R429T/S
(4) T434N and S436T/S
(5) K419N, K421T/S, and G430T/S
(6) K419N, K421T/S, and K427N and R429T/S
(7) K419N, K421T/S, and T434N and S436T/S In particular, it is preferable to add modification of glycosylation by mutagenesis of "K419N, K421T, K427N and R429T", "K419N, K421T and G430T", and "K419N, K421T, T434N and S436T".

The RSV F/G chimeric vaccine comprises a protein derived from an expression system using *E. coli*, lactic acid bacteria, yeast, plant cells, insect cells or animal cells as a host. For example, the protein may be a protein derived from an expression system using *E. coli* (*Escherichia coli*), budding yeast (*Saccharomyces cerevisiae*), *Pichia* yeast (*Pichia pastoris*), fission yeast (*Schizosaccharomyces pombe*), Sf9 cells, Hi-5 cells, Chinese Hamster Ovary (CHO) cells, Baby hamster kidney (BHK) cells, C127 cells, NS0 cells, SP2 cells, MDCK cells, EB66 cells, Vero cells, GL-37 cells, HT-1080 cells, HEK293 cells, human lymphoblasts or human normal diploid fibroblast cells as a host.

The RSV F/G chimeric vaccine can also comprise an adjuvant. The adjuvant may be, for example, poly(I:C), MPL, RC529, GLA, E6020, flagellin, imiquimod, R848, CpG ODN, QS21, TDB, α-Galactosylceramide, aluminum hydroxide, aluminum phosphate, MF59, AS03, AF03, SE, bilosome, AS01, AS02, AS04, AS15, GLA-SE, IC31, CAF01, ISCOMs, or a combination thereof.

The RSV F/G chimeric vaccine can also comprise an additive. The additive may be, for example, an amino acid, saccharides, a surfactant, or a combination thereof.

Dosage form of the RSV F/G chimeric vaccine may be, for example, a liquid form, a powder form (lyophilized powder, dried powder), a capsule form, a tablet, or a frozen state, but is not limited thereto.

The RSV F/G chimeric vaccine can also comprise a pharmaceutically acceptable carrier. Such a carrier may be, for example, saline, buffered saline, dextrose, water, glycerol, isotonic aqueous buffer, emulsifier, pH adjuster, or a combination thereof.

A method for administering the RSV F/G chimeric vaccine may be a method of administering by a syringe, a transdermal patch, a microneedle, an implantable sustained release device, a syringe with a microneedle, a needleless device, a nasal spray, or oral or sublingual route.

Examples of mammals to be inoculated with the RSV F/G chimeric vaccine include mouse, rat, guinea pig, hamster, rabbit, cat, dog, sheep, pig, cow, horse, goat, monkey, human, and the like. The RSV F/G chimeric vaccine of the present invention is most preferably used for a human, and can also be used for pregnant women, infants, children under the age of 5, and adults over the age of 65, in addition to persons of the age of 5 to 64 regardless of gender.

The number of administrations of the RSV F/G chimeric vaccine of the present invention varies depending on the purpose of administration, administration method, and situation of the administration target (gender, age, weight, medical condition), and when administered to a human, the RSV F/G chimeric vaccine may be administered once, twice, or three times.

Hereinafter, the present invention will be described in detail with reference to examples, but the present invention is not limited to these examples at all.

(Materials and Methods of Examples)

1. Cloning, Construction of Plasmids and Expression Vectors

A DNA fragment encoding a sequence comprising amino acid residues 1 to 524 of RSV F protein, a flag tag and a his tag was prepared by outsourcing. Using this fragment DNA as a template, assembly PCR was performed using a mutagenesis primer or an oligo DNA synthesis product, and fragment DNAs encoding a sequence comprising each of RSV WT F (prepared using RSV F protein 1-513 amino acid residues among an amino acid sequence (CAA26143) of hRSV F protein reported in Non-Patent Document 18; SEQ ID NO: 1), RSV post F protein (prepared using RSV F protein 1-513 amino acid residues among an amino acid sequence of SEQ ID No. 1 described in Patent Document 4; SEQ ID NO: 3), and RSV pre F protein (prepared using RSV F protein 1-513 amino acid residues among an amino acid sequence of SEQ ID No. 383 described in Patent Document 5; SEQ ID NO: 4). The RSV pre F was a sequence comprising a trimerization sequence, a his tag sequence, and a Strep tag sequence contained in the sequence described in the same patent document. Note that a sequence comprising a flag tag and a his tag is not contained.) and the RSV F/G chimeric protein were prepared (the RSV F protein was substituted or added to the CCD of SEQ ID NO: 2 or SEQ ID NO: 11 of the RSV G protein, using SEQ ID NO: 1 as a structure. And the RSV F protein was substituted or added to a partial variant of the CCD of SEQ ID NO: 2 of the RSV G protein, using SEQ ID NO: 1 as a structure). The fragment DNA and a pCAGGS1.dhfr.neo vector cleaved by SalI (Patent Document 8, KM Biologics Co., Ltd.) were linked using In-Fusion® HD Cloning Kit (Takara Bio Inc.) to prepare an animal cell expression vector. Plasmid DNA preparation was carried out by cloning using *E. coli* JM109 competent cell (Toyobo Co., Ltd.).

TABLE 1

| | | |
|---|---|---|
| RSV WT F | MELLILKANAITTILTAVTFCFASGQNITEEFYQSTCS<br>AVSKGYLSALRTGWYTSVITIELSNIKENKCNGTDAKV<br>KLIKQELDKYKNAVTELQLLMQSTPATNNRARRELPRF<br>MNYTLNNAKKTNVTLSKKRKRRFLGFLLGVGSAIASGV<br>AVSKVLHLEGEVNKIKSALLSTNKAVVSLSNGVSVLTS<br>KVLDLKNYIDKQLLPIVNKQSCSISNIETVIEFQQKNN<br>RLLEITREFSVNAGVTTPVSTYMLTNSELLSLINDMPI<br>TNDQKKLMSNNVQIVRQQSYSIMSIIKEEVLAYVVQLP<br>LYGVIDTPCWKLHTSPLCTTNTKEGSNICLTRTDRGWF<br>CDNAGSVSFFPQAETCKVQSNRVFCDTMNSLTLPSEVN<br>LCNVDIFNPKYDCKIMTSKTDVSSSVITSLGAIVSCYG<br>KTKCTASNKNRGIIKTFSNGCDYVSNKGVDTVSVGNTL<br>YYVNKQEGKSLYVKGEPIINFYDPLVFPSDEFDASISQ<br>VNEKINQSLAFIRKSDELL | SEQ ID NO. 1 |
| RSV G | MSKNKDQRTAKTLERTWDTLNHLLFISSCLYKLNLKSV<br>AQITLSILAMIISTSLIIAAIIFIASANHKVTPTTAII<br>QDATSQIKNTTPTYLTQNPQLGISPSNPSEITSQITTI<br>LASTTPGVKSTLQSTTVKTKNTTTTQTQPSKPTTKQRQ<br>NKPPSKPNNDFHFEVFNFVPCSICSNNPTCWAICKRIP<br>NKKPGKKTTTKPTKKPTLKTTKKDPKPQTTKSKEVPTT<br>KPTEEPTINTTKTNIITTLLTSNTTGNPELTSQMETFH<br>STSSEGNPSPSQVSTTSEYPSQPSSPPNTPRQ | SEQ ID NO. 2 |
| RSV post F | MELLILKANAITTILTAVTFCFASGQNITEEFYQSTCS<br>AVSKGYLSALRTGWYTSVITIELSNIKKNKCNGTDAKV<br>KLIKQELDKYKNAVTELQLLMQSTPATNNRARRELPRF<br>MNYTLNNAKKTNVTLSKKRKRRFLGFLLGVGSAIASGV<br>AVSKVLHLEGEVNKIKSALLSTNKAVVSLSNGVSVLTS<br>KVLDLKNYIDKQLLPIVNKQSCSISNIETVIEFQQKNN<br>RLLEITREFSVNAGVTTPVSTYMLTNSELLSLINDMPI<br>TNDQKKLMSNNVQIVRQQSYSIMSIIKEEVLAYVVQLP<br>LYGVIDTPCWKLHTSPLCTTNTKEGSNICLTRTDRGWY | SEQ ID NO. 3 |

TABLE 1-continued

| | | |
|---|---|---|
| | CDNAGSVSFFPQAETCKVQSNRVFCDTMNSLTLPSEVN<br>LCNVDIFNPKYDCKIMTSKTDVSSSVITSLGAIVSCYG<br>KTKCTASNKNRGIIKTFSNGCDYVSNKGVDTVSVGNTL<br>YYVNKQEGKSLYVKGEPIINFYDPLVFPSDEFDASISQ<br>VNEKINQSLAFIRKSDELL | |
| RSV pre F | MELLILKANAITTILTAVTFCFASGQNITEEFYQSTCS<br>AVSKGYLSALRTGWYTSVITIELSNIKENKCNGTDAKV<br>KLIKQELDKYKNAVTELQLLMQSTPATNNRARRELPRF<br>MNYTLNNAKKTNVTLSKKRKRRFLGFLLGVGSAIASGV<br>AVCKVLHLEGEVNKIKSALLSTNKAVVSLSNGVSVLTF<br>KVLDLKNYIDKQLLPILNKQSCSISNIETVIEFQQKNN<br>RLLEITREFSVNAGVTTPVSTYMLTNSELLSLINDMPI<br>TNDQKKLMSNNVQIVRQQSYSIMCIIKEEVLAYVVQLP<br>LYGVIDTPCWKLHTSPLCTTNTKEGSNICLTRTDRGWY<br>CDNAGSVSFFPQAETCKVQSNRVFCDTMNSLTLPSEVN<br>LCNVDIFNPKYDCKIMTSKTDVSSSVITSLGAIVSCYG<br>KTKCTASNKNRGIIKTFSNGCDYVSNKGVDTVSVGNTL<br>YYVNKQEGKSLYVKGEPIINFYDPLVFPSDEFDASISQ<br>VNEKINQSLAFIRKSDELL | SEQ ID NO.<br>4 |
| GGGGS<br>Linker | GGGGS | SEQ ID NO.<br>5 |
| EAAAK<br>Linker | EAAAK | SEQ ID NO.<br>6 |
| RSVB G<br>(158-199) | KPKDDYHFEVFNFVPCSICGNNQLCKSICKTIPSNKPK<br>KKPT | SEQ ID NO.<br>11 |

2. Expression and Purification

2-1. Transfection

Expi293 cells (Thermo Fisher Scientific) were prepared into a tube so as to be $7.5 \times 10^7$ viable cells, and centrifuged (1000 rpm, 5 min, RT). After removal of the supernatant, the cells were suspended in 25.5 mL of previously warmed Expi293 Expression Medium and transferred to a 125 mL flask. A solution in which 30 µg of plasmid DNA was added to OPTI-MEM and mixed by pipetting and a solution in which 80 µL of ExpiFectamine 293 solution was added to Opti-MEM and incubated at room temperature for 5 minutes were mixed and incubated at room temperature for 20 to 30 minutes. The DNA-Expi293 complex was added dropwise to the flask into which the Expi293 cells were transferred. The mixture was stirred and cultured using a CO2 incubator (Thermo Fisher Scientific) under conditions of 37° C., $CO_2$ 8%, and 125 rpm. Sixteen to eighteen hours after transfection, 150 µL of Transfection Enhancer 1 and 1.5 mL of Transfection Enhancer 2 were added thereto, and the mixture was stirred and cultured using a CO2 incubator under the conditions of 37° C., $CO_2$ 8%, and 125 rpm. After culturing for 2 to 7 days, the cells were harvested, centrifuged (2500 rpm, 5 min, 4° C.) and then filtered to 0.22 µm, and the supernatant was collected.

2-2. Affinity Purification

Ni-NTA Agarose (Qiagen) was dispensed in 1 mL, and the mixture was washed three times with 5 mL of D-PBS (Wako Pure Chemical Industries, Ltd.). A sample was added to the pretreated Ni-NTA Agarose and collected in a 50 mL tube. The mixture was rotated at 4° C. for 16 to 18 hours and transferred to columns, and washed with D-PBS and Wash buffer 2 (50 mM Tris-HCl (pH 7.4), 500 mM NaCl, 25 mM imidazole). Thereafter, an elution buffer (50 mM Tris-HCl (pH 7.4), 500 mM NaCl, 25 to 500 mM imidazole) was added to collect the eluted fraction. The protein concentration was measured, and the protein elution peak sample was dialyzed with D-PBS. After dialysis and recovery, filtration was performed with a 0.22 µm filter.

3. Adjuvant

Adju-Phos® (BRENNTAG), an aluminum phosphate gel, was prepared so as to be 6 µg/mouse and used.

4. Cells

Vero cells, Hep-2 cells (CCL-23, ATCC), and Expi293 cells (Expi293F™, Thermo Fisher Scientific) were passaged by the manufacturer's recommended method, and used for each test and antigen preparation.

5. Mice

Female BALB/c mice with SPF (Japan SLC, Inc.) were conditioned for about one week, and then used for an immunogenicity test, a test in protection against infection, and the like.

6. Viruses

RSV A2 (VR-1540, ATCC) was propagated by the manufacturer's recommended method. The prepared virus was stored at −80° C. for a period of time until use.

7. SDS-PAGE and Western Blot

7-1. SDS-PAGE

A specimen was added to a mixed liquid of sample buffer and DTT, and after heat treatment (96° C., 3 to 5 min), SDS-PAGE was performed using SDS-PAGE mini (TEFCO) or Bolt®Bis-Tris gel (Thermo Fisher Scientific). After electrophoresis, they were stained with Bullet CBB Stain One (Nacalai) and moderately decolorized with deionized water. The gel was photographed with LAS-3000 (FUJIFILM Corporation) or WSE-6100 LuminoGraph I (Atto).

7-2. Western Blot

After electrophoresis was performed by the above method, a membrane was treated with methanol, and blotting was performed using a semi-dry blotting apparatus. The extracted membrane was blocked with 5% skim milk for 30 minutes. After washing with PBST, a diluted anti-RSV F antibody and the membrane were reacted for 1 hour. After washing with PBST, a diluted anti-mouse IgG antibody (Thermo Fisher Scientific) and the membrane were reacted for 1 hour. After washing with PBST, Western BLoT Ultra Sensitive HRP Substrate (Takara Bio Inc.) and the membrane were reacted. The membranes subjected to the above treatment were photographed with LAS-3000 (FUJIFILM Corporation).

8. Gel Filtration Chromatography (GFC)

Particle diameter was measured using size exclusion chromatography. A specimen diluted with D-PBS and then filtered through a 0.22 μm filter was measured using a system of Agilent 1200 Series (Agilent Technologies) and a column of Superdex® 200 Increase 5/150 GL (GE Healthcare). The molecular weight was analyzed using Gel Filtration Standard (Bio-Rad) as a standard.

9. Particle Size Measurement by Dynamic Light Scattering (DLS)

Particle sizes of various proteins were measured using a Zetasizer Nano (Malvern Panalytical). The measurement was performed according to manufacturer's instruction.

10. Electron Microscope

Observation was performed using TecnaiG2 12 TWIN (FEI Company) by negative staining method with saturated uranium acetate and 2% PTA (phosphotungstic acid).

11. ELISA 11-1. Sandwich ELISA

An anti-RSV F antibody diluted with D-PBS was applied to a 96 well MAXSORP plate (Thermo Fisher Scientific), and the plate was allowed to stand at 2 to 8° C. overnight or at 37° C. for 1 hour. The antibody diluent was removed from the plate on which the anti-RSV F antibody had been immobilized, then the plate was washed with PBS, 1% BSA was applied, and the plate was allowed to stand for 1 hour. The blocking liquid was removed, the specimen was applied and sealed, and then the plate was allowed to stand at 37° C. for 1 hour. After removing the specimen, the plate was washed with PBST, a biotinylated anti-RSV F antibody diluted with 1% BSA was applied and sealed, and then the plate was allowed to stand at 37° C. for 1 hour. After removing the biotinylated anti-RSV F antibody solution, the plate was washed with PBST, diluted HRP-labeled streptavidin (VECTOR Laboratories) was applied and sealed, and then the plate was allowed to stand at 37° C. for 1 hour. After removing the HRP-labeled streptavidin solution, the plate was washed with PBST, 3,3',5,5'-Tetramethylbenzidine Liquid Substrate, Supersensitive, for ELISA-ready to use solution (Sigma-Aldrich) was applied, and the plate was allowed to stand at room temperature for 30 minutes. 1 N $H_2SO_4$ was applied to the plate to stop color development, and then measurement was made with SPECTRAMAX190 (Thermo Fisher Scientific).

11-2. Indirect ELISA

RSV F protein diluted with D-PBS was applied to well Pierce Nickel Coated Plate (Thermo Fisher Scientific), and the plate was allowed to stand at 2 to 8° C. overnight or at 37° C. for 1 hour. After removing the RSV F protein diluent, the plate was washed with PBS, 1% BSA was applied, and the plate was allowed to stand for 1 hour. The blocking liquid was removed, the specimen was applied and sealed, and then the plate was allowed to stand at 37° C. for 1 hour. After removing the specimen, the plate was washed with PBST, and an anti-mouse IgG HRP-labeled antibody or an anti-human IgG HRP-labeled antibody diluted with 1% BSA was applied and sealed, and then the plate was allowed to stand at 37° C. for 1 hour. After removing the HRP-labeled antibody diluent, the plate was washed with PBST, 3,3',5,5'-Tetramethylbenzidine Liquid Substrate, Supersensitive, for ELISA-ready to use solution (Sigma-Aldrich) was applied, and the plate was allowed to stand at room temperature for 30 minutes. 1 N $H_2SO_4$ was applied to the plate to stop color development, and then measurement was made with SPECTRAMAX190 (Thermo Fisher Scientific).

12. Real-Time PCR 12-1. RNA Extraction and cDNA Synthesis

BALF (bronchoalveolar lavage fluid) collected in the infection protection test was centrifuged (300 g or 1500 rpm), and then the supernatant was collected. Viral RNA was separated from 150 μL of the supernatant using NucleoSpin® RNA Virus (MACHEREY-NAGEL). The protocol was performed by the manufacturer's recommended method. cDNA synthesis was performed from RNA extracted using High-Capacity cDNA Reverse Transcription Kit (Applied Biosystems). The protocol was performed by the manufacturer's recommended method.

12-2. PCR

A sense primer (RSVf-F, SEQ ID NO: 7), an antisense primer (RSVf-R, SEQ ID NO: 8), an MGB probe (RSVfA-TaqPf-FAM, SEQ ID NO: 9 with modifications of [FAM] and [MGBEQ]), a Distilled Water (NIPPON GENE CO., LTD.) and a specimen were mixed to prepare a specimen solution, and standard DNA (SEQ ID NO: 10) was used to have $10^2$ to $10^7$ copies to prepare a standard solution. The primer, probe, and standard DNA were prepared by outsourcing with reference to Non-Patent Document 20. Real-time PCR was performed by <50° C., 2 min> followed by cycles of <95° C., 10 min>→<95° C., 30 sec>→<60° C., 1 min>50 times. A calibration curve was prepared from an amplification curve of the standard solution, and viral copy number of the specimen was calculated.

TABLE 2

| sense primer (RSVf-F) | CARCAAAGTTAYTCTATCATGTC | SEQ ID NO. 7 |
|---|---|---|
| antisense primer (RSVf-R) | GATCCTGCATTRTCACARTACCA | SEQ ID NO. 8 |
| MGB probe (RSVfA-TaqPf-FAM) | TGTAGTACAATTRCCACT | SEQ ID NO. 9 |
| standard DNA | TGTCCAACAATGTTCAAATAGTTAGACAGCAA AGTTACTCTATCATGTCCATAATAAAAGAGGA AGTCTTAGCATATGTAGTACAATTACCACTAT ATGGTGTTATAGATACACCCTGTTGGAAACTA CACACATCCCCTCTATGTACAACCAACACAAA AGAAGGGTCCAACATCTGTTTAACAAGAACTG ACAGAGGATGGTACTGTGACAATGCAGGATCA GTATCTTTCTTCCCACAAGCTGAAACATGTA | SEQ ID NO. 10 |

DNA sequences are described in 5' → 3' direction.
Y represents a mixed nucleotide of "C or T" and R represents "G or A".
Note that a labeled fluorescent dye [FAM] is modified on the 5' side of the MGB probe (SEQ ID NO: 9), and Minor Groove Binder (MGB) and Eclipse quencher (EQ) [MGBEQ] are modified on the 3' side.

13. Immunogenicity Test

Specimens prepared so as to be 5 μg/mouse were intramuscularly administered to female BALB/c aged 6 to 7 weeks twice at intervals of 3 weeks, and after 3 weeks, whole blood was collected under isoflurane anesthesia. Serum was separated to collect serum, immunogenicity was evaluated by indirect ELISA, neutralizing capacity was evaluated by a neutralization test, and complement-dependent neutralizing capacity was evaluated by a complement-dependent neutralization test.

14. Neutralization Test

Hep-2 Cells were seeded at $2 \times 10^5$ cells/mL in a 96 well plate, and cultured under conditions of 37° C., 5% $CO_2$ for 1 day. The serum diluted with a medium and an RSV diluent were mixed in equal amounts, and the mixture was allowed to stand under the conditions of 37° C., 5% $CO_2$ for 1 hour. After removing the culture supernatant of the plate, the serum-RSV reaction solution was added, and cultured under the conditions of 37° C., 5% $CO_2$ for 3 to 5 days. After removing the reaction solution, the plate was washed with PBS, methanol was added thereto, and the plate was allowed to stand at room temperature for 30 minutes. After methanol was removed and the plate was air dried, the plate was washed with PBS, an anti-RSV F antibody diluent was applied, and then the plate was allowed to stand at 37° C. for 1 hour. After removing the anti-RSV F antibody diluent, an anti-mouse IgG Alexa 488 labeled antibody (Abcam) diluent was applied, and the plate was allowed to stand at 37° C. for 1 hour. After removing the anti-mouse IgG Alexa 488 labeled antibody (Abcam) diluent, the plate was washed with PBS, a diluted Hoechst 33342 solution (DOJINDO LABORATORIES) was applied, and the plate was allowed to stand in the dark for 10 minutes. After removing a nuclear stain and washing with PBS, PBS was applied to the plate and analyzed with an image analyzer. Based on infection rates of the serum dilution series, curve fitting was performed using GraphPad Prism 7 (GraphPad Software) according to fitting guide using an infection rate of the well to which only RSV was applied as a reference, and a neutralizing antibody titer (IC50) was calculated.

15. Complement-Dependent Neutralization Test

Cells were prepared as in the neutralization test. A medium comprising 1/50 amount of rabbit serum complement (Cedarlane) was used for RSV dilution. The serum diluted with a medium and an RSV diluent were mixed in equal amounts, and the mixture was allowed to stand under the conditions of 37° C., 5% $CO_2$ for 1 hour. The serum-RSV reaction solution was added, and cultured under the conditions of 37° C., 5% $CO_2$ for 1 hour. Thereafter, the serum-RSV reaction solution was removed, the plate was washed with PBS, a complement-free medium was added, and the mixture was cultured under the conditions of 37° C., 5% $CO_2$ for 3 to 5 days. Other operations and analysis were performed according to the method of the neutralization test.

16. Subclass Analysis

The same procedure as in the indirect ELISA method was carried out except that an anti-mouse IgG1 HRP-labeled antibody (Abcam) and an anti-mouse IgG2a HRP-labeled antibody (Abcam) were used as secondary antibodies.

17. Test in Protection Against Infection

A specimen prepared to be 0.005 to 15 µg/mouse was intramuscularly administered to female BALB/c aged 6 to 7 weeks twice at intervals of 3 weeks, and then after 3 weeks, $1\times10^5$ pfu/mouse of RSV was intranasally inoculated under isoflurane anesthesia. Three to four days after infection, BALF was collected after euthanization with carbon dioxide gas. RNA was extracted from BALF to synthesize cDNA, and viral copy number was detected by real-time PCR.

18. Evaluation of Infection Enhancement

Enhancement of infection or infection suppressing ratio was evaluated with reference to a geometric mean of viral copy numbers in BALF of a group immunized with physiological saline and challenged with RSV. In addition, the geometric mean of viral copy numbers in the lung of the RSV-challenged group was evaluated with reference to a group into which a serum obtained by immunization with physiological saline was transferred. The serum transfer was performed by intraperitoneal administration at 400 uL/mouse, using various sera diluted by $10^8$, in which exacerbation confirmed by preparing a dilution series in advance becomes a peak. One day after serum transfer, $1\times10^5$ pfu/mouse of RSV was intranasally inoculated under isoflurane anesthesia. Three to four days after infection, lungs were collected after euthanization with carbon dioxide gas. RNA was extracted from the lungs to synthesize cDNA, and the viral copy number was detected by real-time PCR.

19. Statistical Analysis

Statistical analysis was performed using GraphPad Prism 7 (GraphPad Software).

Example 1

Preparation of RSV F/G Chimeric Proteins

Various RSV F/G chimeric proteins shown in FIGS. 1 to 4 were expressed in Expi293 cells and then purified with an affinity column. Each protein yield was shown in FIGS. 5 and 6. A protein to which mutation was added so as to add a sugar chain to a specific position tended to have a high expression level as compared with a protein to which a sugar chain was not added. Specifically, the expression levels of the F/G chimeric proteins to which a sugar chain was added by mutagenesis in "K419N, K421T and G430T", "K419N, K421T, T434N and S436T", and "K419N, K421T, K427N and R429T" increased.

Example 2

Evaluation of Physical Properties

1. SDS-PAGE and Western Blot

The results of analyzing each protein by SDS-PAGE and Western blot are shown in FIGS. 7 to 15, and 27 to 39. By comparing the results of SDS-PAGE and Western blot, it was confirmed that a main band was an RSV F/G chimeric protein.

Figure 7:
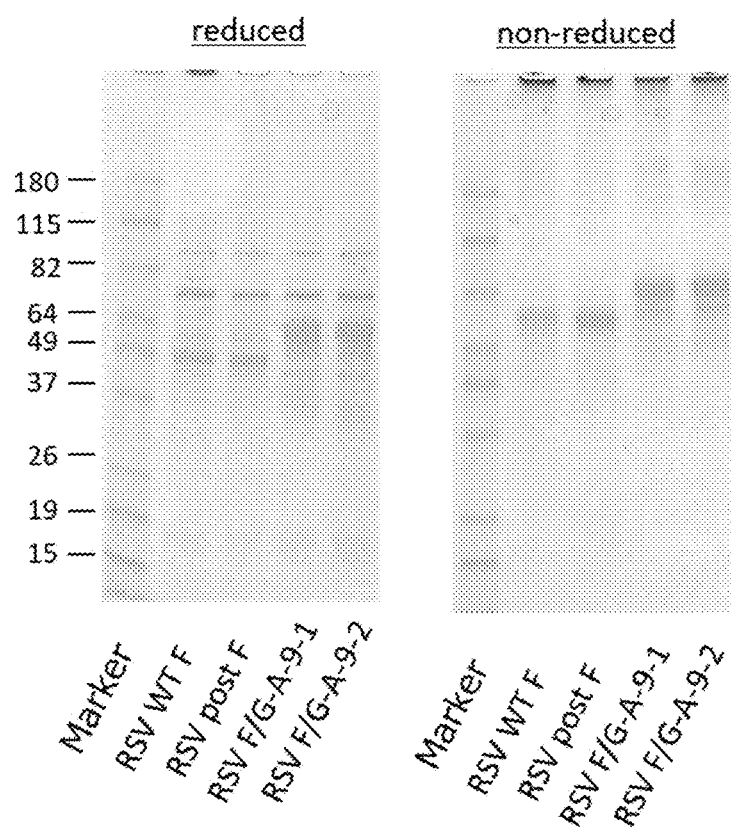
FIG. 7 shows the results of SDS-PAGE of RSV F/G chimeric proteins.
Figure 8:
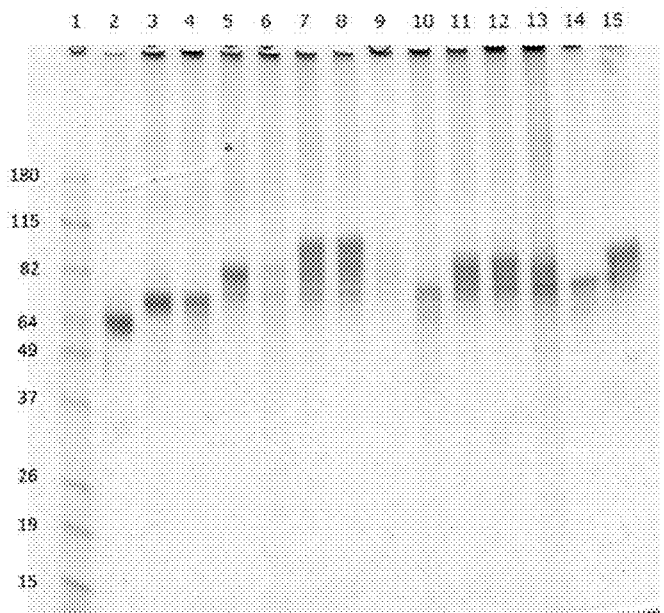
FIG. 8 shows the results of SDS-PAGE of RSV F/G chimeric proteins.
Figure 9:
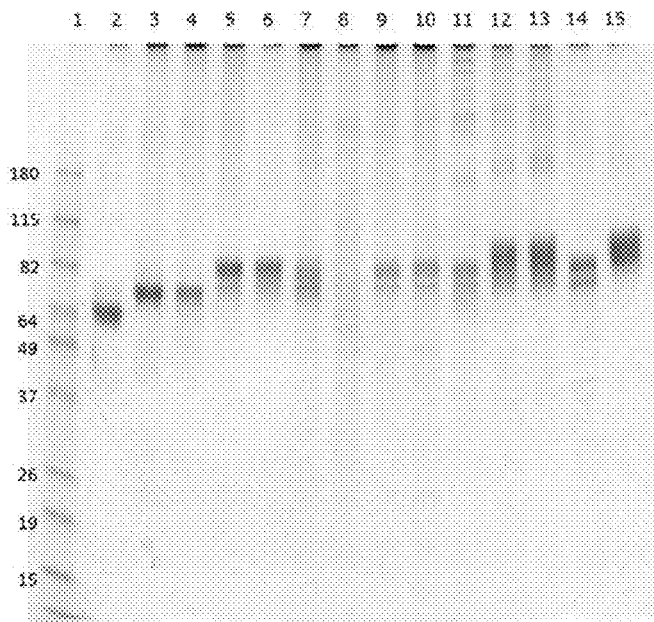
FIG. 9 shows the results of SDS-PAGE of RSV F/G chimeric proteins.
Figure 12:
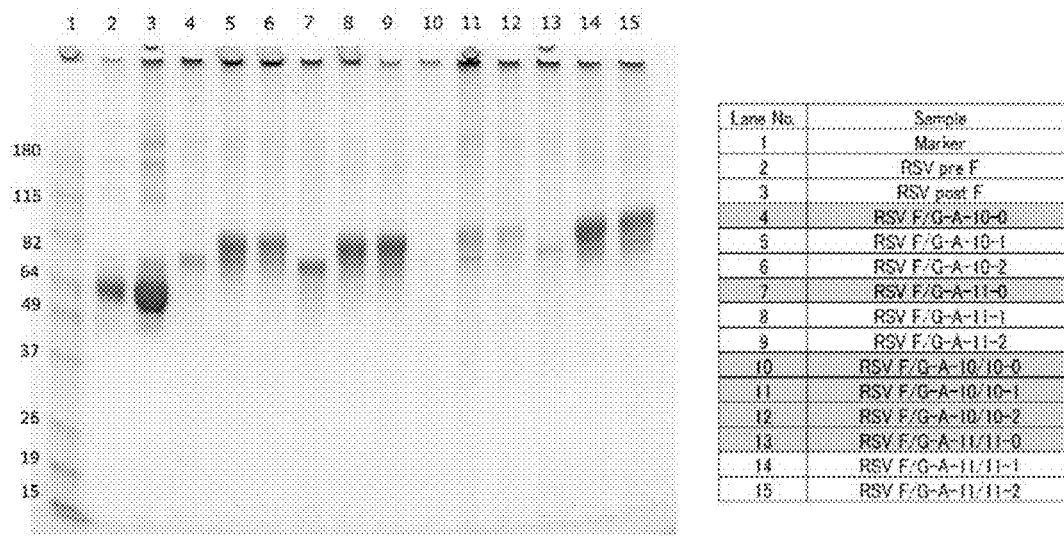
FIG. 12 shows the results of SDS-PAGE of RSV F/G chimeric proteins.
Figure 13:
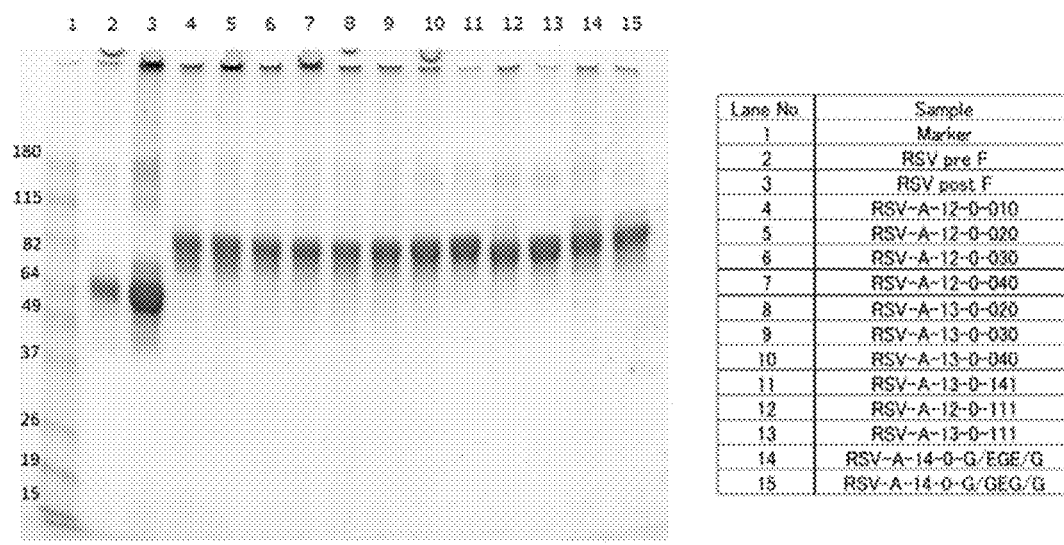
FIG. 13 shows the results of SDS-PAGE of RSV F/G chimeric proteins.
Figure 14:
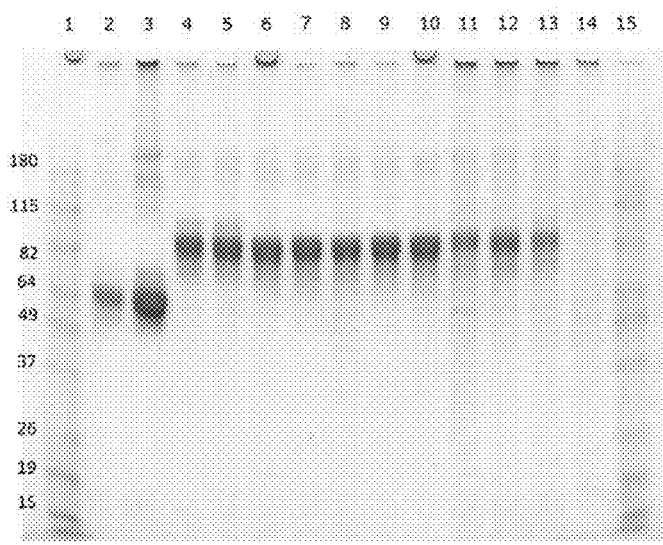
FIG. 14 shows the results of SDS-PAGE of RSV F/G chimeric proteins.
Figure 15:
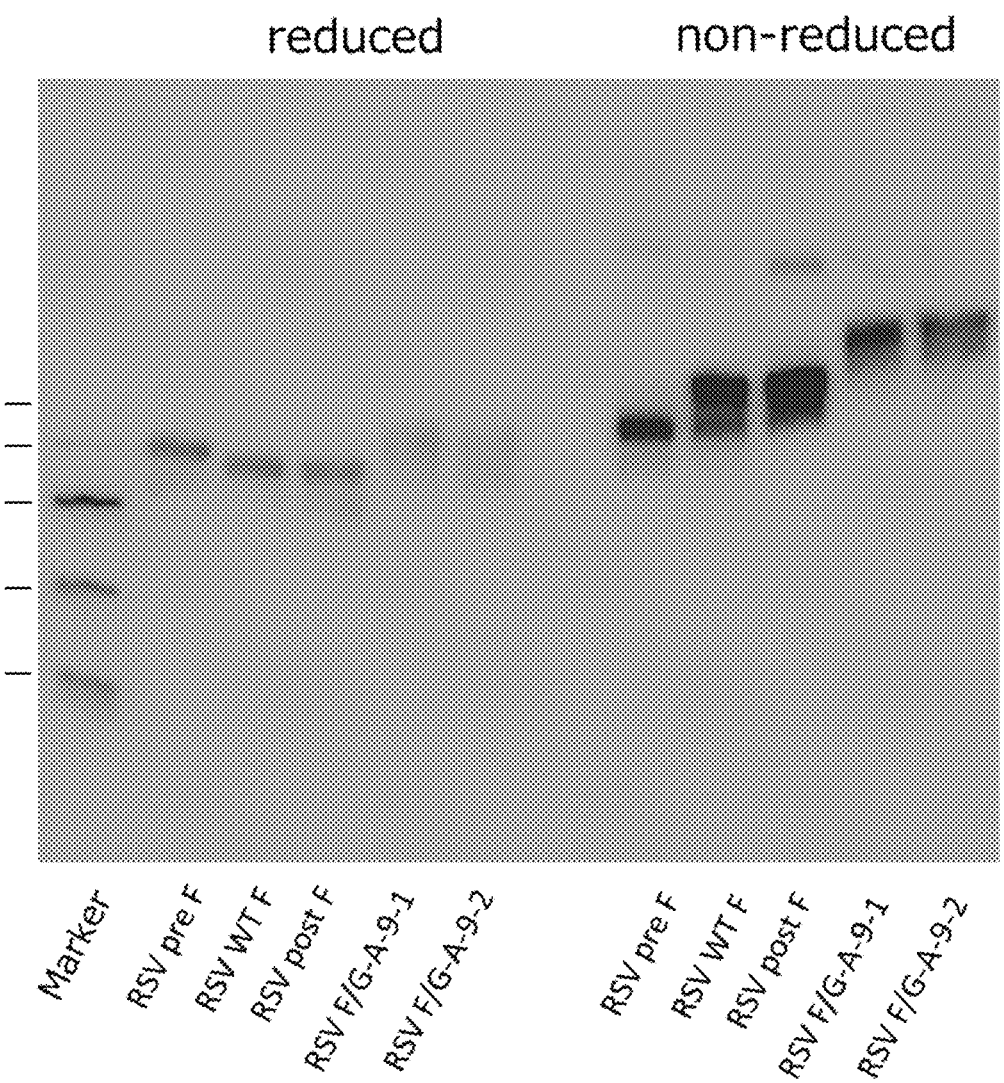
FIG. 15 shows the results of Western blot of RSV F/G chimeric proteins.

The results of SDS-PAGE of RSV F/G-A-9-1 and RSV F/G-A-9-2 substituted with 10-amino acid sequence (162 to 171; No. 9 in FIG. 2) of RSV G protein comprising a region (164 to 171) that is a particularly highly conserved region and does not comprise Cysteine noose (characteristic structure formed by disulfide bonds between cysteine residues 173 to 186 and between 176 to 182) among sequences of region CCD having high homology between virus strains, among the RSV F/G chimeric proteins, are shown in FIG. 7. Wild-type RSV F protein (593 aa) was 62 kDa, and it was confirmed that main bands of RSV WT F protein (513 aa) and RSV post F protein (513 aa), which are glycoproteins, were observed at positions higher than around estimated molecular weight. Also, the fact that a main band of the RSV F/G chimeric protein (513 aa) is located at a higher position than the WT and post F proteins is suggested to be due to an effect of glycosylation by mutagenesis.

The results of SDS-PAGE (non-reduced) of various RSV F/G proteins are shown in FIGS. 8 to 14. For Sample in which the application amount is less than 1 µg/Lane due to a small expression level, Lane No. and Sample are shown in gray. Among the RSV F/G chimeric proteins to which mutation to add a sugar chain to the position shown in FIG. 1 was not added, RSV F/G-A-1-0, RSV F/G-A-2-0, RSV F/G-A-3-0, RSV F/G-A-4-0, RSV F/G-A-8-0, RSV F/G-A-5-0, RSV F/G-A-10-0, RSV F/G-A-11-0, and RSV F/G-A-11/11-0 resulted in that a main band could not be confirmed, intensity was low, or the expression level was low. In addition, main bands and high expression levels could be confirmed for RSV F/G-A-1-1, RSV F/G-A-1-2, RSV F/G-

A-2-1, RSV F/G-A-2-2, RSV F/G-A-3-1, RSV F/G-A-3-2, RSV F/G-A-6-1, RSV F/G-A-6-2, RSV F/G-A-7-1, RSV F/G-A-7-2, RSV F/G-A-8-1, RSV F/G-A-8-2, RSV F/G-A-5-1, RSV F/G-A-5-2, RSV F/G-A-9-1, RSV F/G-A-9-2, RSV F/G-A-10-1, RSV F/G-A-10-2, RSV F/G-A-11-1 and RSV F/G-A-11-2 to which the mutation of "K419N, K421T and G430T" and the glycosylation mutation of "K419N, K421T, T434N and S436T" were added, whereas RSV F/G-A-1-3, RSV F/G-A-2-3 and RSV F/G-A-9-3 to which the glycosylation mutation of "K421T and G430T" was added had low main band intensities or low expression levels as compared with the mutation of "K419N, K421T and G430T" and the glycosylation mutation of "K419N, K421T, T434N and S436T".

2. Gel Filtration Chromatography Analysis (GFC)

Size analysis of each protein was performed using gel filtration chromatography. The results of GFC are shown in Table 3. It was found that the RSV F/G-A-9-1 and the RSV F/G-A-9-2 had a protein with a size of 670 kDa or more (extrapolated value is shown when the size is 670 kDa or more) as a main peak and a protein with a size of about 120 kDa as a second peak. The wild-type RSV F protein is known to form a trimer as a natural structure, and when the RSV F/G-A-9-1 and the RSV F/G-A-9-2 are assumed to similarly form a trimer, it was suggested that the RSV F/G-A-9-1 and the RSV F/G-A-9-2 similarly form a trimer because they have molecular weights close to that of the second peak. In addition, it is suggested that the main peak showed a size of 670 kDa or more because the trimers of RSV F/G-A-9-1 and RSV F/G-A-9-2 form a rosette-like structure as in the electron microscope image described later.

TABLE 3

List of GFC results

| Sample | main peak (Mw.) | second peak |
| --- | --- | --- |
| RSV pre F | 307,507 | 1,086,954 |
| RSV post F | 1,219,027 | — |
| RSV WT F | 1,327,282 | — |
| RSV F/G-A-1-0 | 1,150,389 | — |
| RSV F/G-A-1-1 | 1,123,751 | 159,575 |
| RSV F/G-A-1-2 | 1,116,844 | 163,157 |
| RSV F/G-A-1-3 | 1,170,420 | — |
| RSV F/G-A-2-0 | 1,199,642 | 103,643 |
| RSV F/G-A-2-1 | 1,211,534 | 140,716 |
| RSV F/G-A-2-2 | 1,213,029 | 163,560 |
| RSV F/G-A-2-3 | 1,141,909 | 137,627 |
| RSV F/G-A-3-0 | 1,231,111 | 102,625 |
| RSV F/G-A-3-1 | 1,238,725 | — |
| RSV F/G-A-3-2 | 1,235,674 | — |
| RSV F/G-A-3-3 | 1,205,574 | 135,606 |
| RSV F/G-A-4-0 | 1,164,661 | 1,244 |
| RSV F/G-A-4-1 | 1,170,420 | 1,118 |
| RSV F/G-A-4-2 | 1,166,098 | 1,234 |
| RSV F/G-A-6-0 | 1,070,990 | 112,291 |
| RSV F/G-A-6-1 | 1,048,773 | 153,970 |
| RSV F/G-A-6-2 | 1,055,259 | 151,896 |
| RSV F/G-A-7-0 | 1,008,197 | — |
| RSV F/G-A-7-1 | 1,076,285 | 139,163 |
| RSV F/G-A-7-2 | 1,107,245 | — |
| RSV F/G-A-8-0 | 1,156,077 | 2,204 |
| RSV F/G-A-8-1 | 1,108,612 | 158,790 |
| RSV F/G-A-8-2 | 1,119,601 | 158,595 |
| RSV F/G-A-5-1 | 1,157,503 | 136,109 |
| RSV F/G-A-5-2 | 1,151,808 | 138,821 |
| RSV F/G-A-5-3 | 1,163,226 | 131,977 |
| RSV F/G-A-9-0 Δ136aa | 1,177,658 | 122,263 |
| RSV F/G-A-9-4 Δ136aa | 1,168,977 | 149,112 |
| RSV F/G-A-9-1 Δ136aa | 1,147,555 | 166,202 |

TABLE 3-continued

List of GFC results

| Sample | main peak (Mw.) | second peak |
| --- | --- | --- |
| RSV F/G-A-9-2 Δ136aa | 1,144,729 | 165,181 |
| RSV F/G-A-9-3 Δ136aa | 1,158,931 | 157,620 |
| RSV WT F-R136Q | 1,158,931 | 127,184 |
| RSV post F-R136Q | 1,105,881 | 128,287 |
| RSV F/G-A-9-0-R136Q | 1,139,097 | 459,085 |
| RSV F/G-A-9-0 | 1,182,022 | 100,126 |
| RSV F/G-A-9-4 | 1,146,141 | 129,399 |
| RSV F/G-A-9-3 | 1,176,207 | 139,507 |
| RSV F/G-A-9-1 | 1,179,111 | 139,679 |
| RSV F/G-A-9-2 | 1,167,537 | 139,335 |

3. Particle Size Measurement by Dynamic Light Scattering (DLS)

Particle diameter of each protein was measured by dynamic light scattering. Average particle diameter of each protein is shown in Table 4.

TABLE 4

List of DLS results

| Sample | Peak | Diameter (nm) | Volume (%) |
| --- | --- | --- | --- |
| RSV pre F | 1 | 13.94 | 99.6 |
|  | 2 | 491.5 | 0.2 |
|  | 3 | 4668 | 0.2 |
| RSV post F | 1 | 37.31 | 99.0 |
|  | 2 | 717.6 | 0.6 |
|  | 3 | 4011 | 0.4 |
| RSV F/G-A-9-1 | 1 | 29.81 | 99.7 |
|  | 2 | 4013 | 0.3 |
|  | 3 | 0.000 | 0.0 |
| RSV F/G-A-9-2 | 1 | 29.58 | 99.8 |
|  | 2 | 4190 | 0.2 |
|  | 3 | 0.000 | 0.0 |

4. Analysis by Electron Microscope

Figure 16:
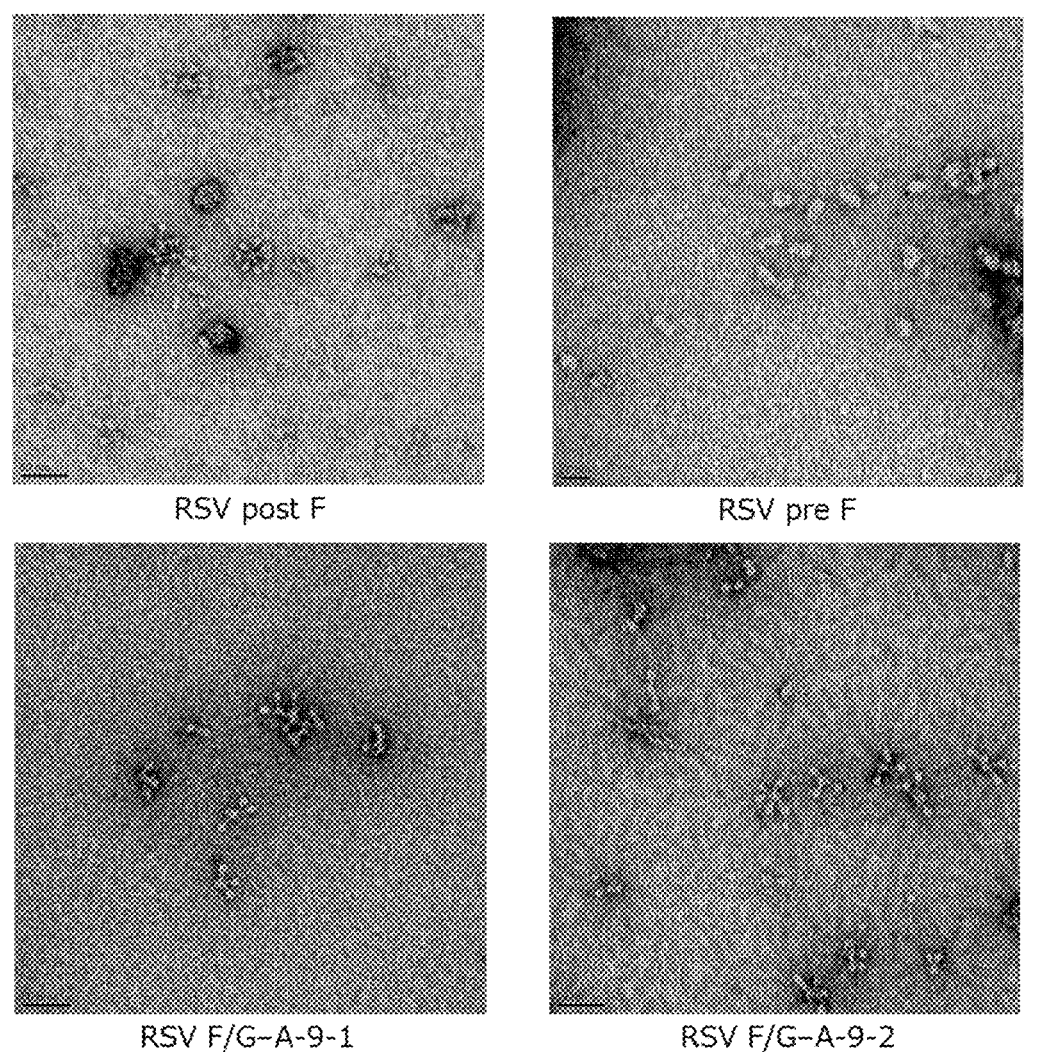

Shape of the RSV F/G chimeric protein was observed with an electron microscope. Electron microscope images of RSV F/G-A-9-1, RSV F/G-A-9-2, RSV post F, and RSV pre F are shown in FIG. 16. It was suggested that the RSV F/G-A-9-1 and the RSV F/G-A-9-2 formed a rosette-like structure similar to that of the RSV post F.

Example 3

Analysis of Reactivity with Anti-RSV F Antibody

Reactivity (indicated by absorbance) between each protein and an anti-RSV F antibody was analyzed by indirect ELISA method. The results of analysis of RSV F protein with anti-RSV F antibodies specific to each site of siteφ, siteI, siteII, siteIII, and siteIV (Non-Patent Document 23) are shown in FIG. 17, FIG. 18, FIG. 40, and FIG. 41. A difference in reactivity with various antibodies was observed, depending on the substituted RSV G protein sequence and the glycosylation mutation. Among the proteins to which glycosylation mutation was added around siteIV, reduced reactivity with the anti-RSV F siteIV antibody was observed. Coincidentally, a plurality of RSV F/G chimeric proteins substituted with RSV G protein that had increased reactivity with an RSV pre F-specific antibody as compared with the RSV WT F were observed.

Example 4

Neutralization Test

Figure 19:
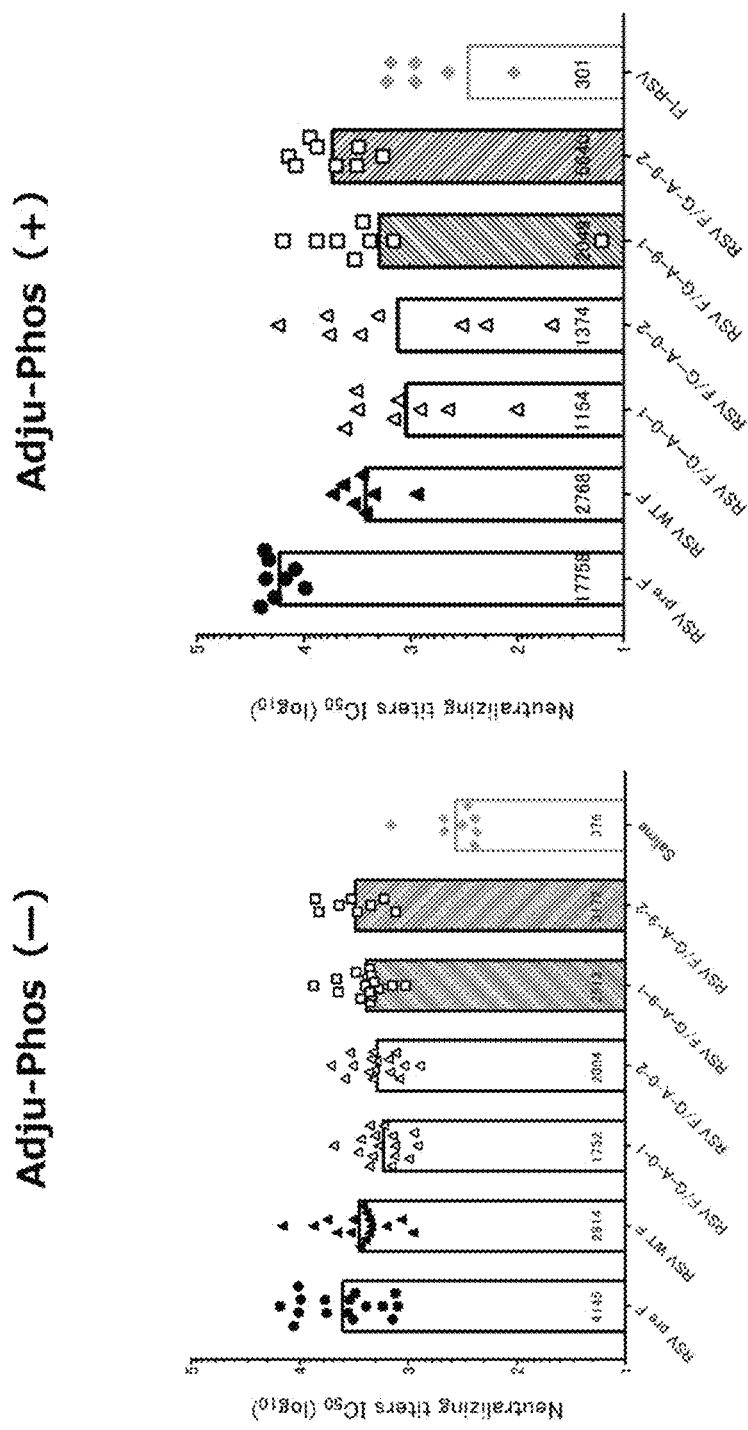
FIG. 19 shows the results of neutralization test of RSV F/G chimeric protein immune sera.

Each protein was immunized to obtain serum, and a neutralization test was carried out. The neutralization test was performed by setting an administration group using Adju-Phos® (BRENNTAG) which is an alum phosphate adjuvant and a group without adjuvant. The results of the neutralization test are shown in FIG. 19. The neutralizing antibody titer (IC50, geometric mean) tended to be high in the RSV F/G-A-9-1 and RSV F/G-A-9-2 comprising the RSV G protein sequence as compared with RSV F/G-A-0-1 and RSV F/G-A-0-2 that are different only in comprising no RSV G protein sequence. In addition, the neutralizing antibody titer (IC50, geometric mean) was the highest in RSV pre F, followed by RSV F/G-A-9-2 and WT in this order. The neutralizing antibody titer of the RSV F/G-A-9-1 was comparable to that of the RSV WT F, and the RSV F/G-A-0-1 and the RSV F/G-A-0-2 showed neutralizing antibody titers (IC50, geometric mean) below the RSV WT F.

Example 5

Complement-Dependent Neutralization Test

Figure 20:
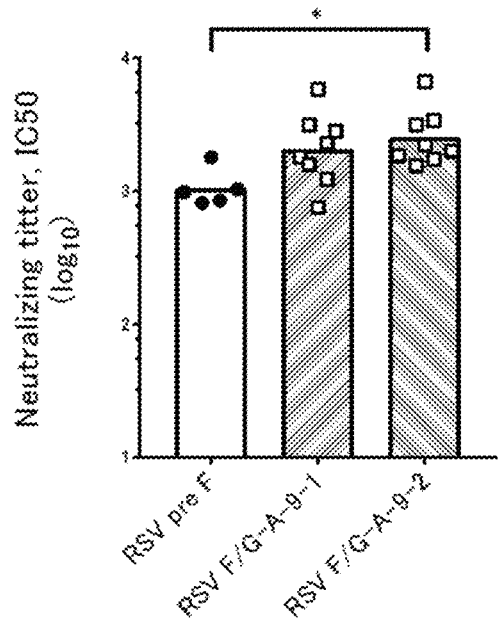
FIG. 20 shows the results of complement-dependent neutralization test of RSV F/G chimeric protein immune sera.
Figure 42:
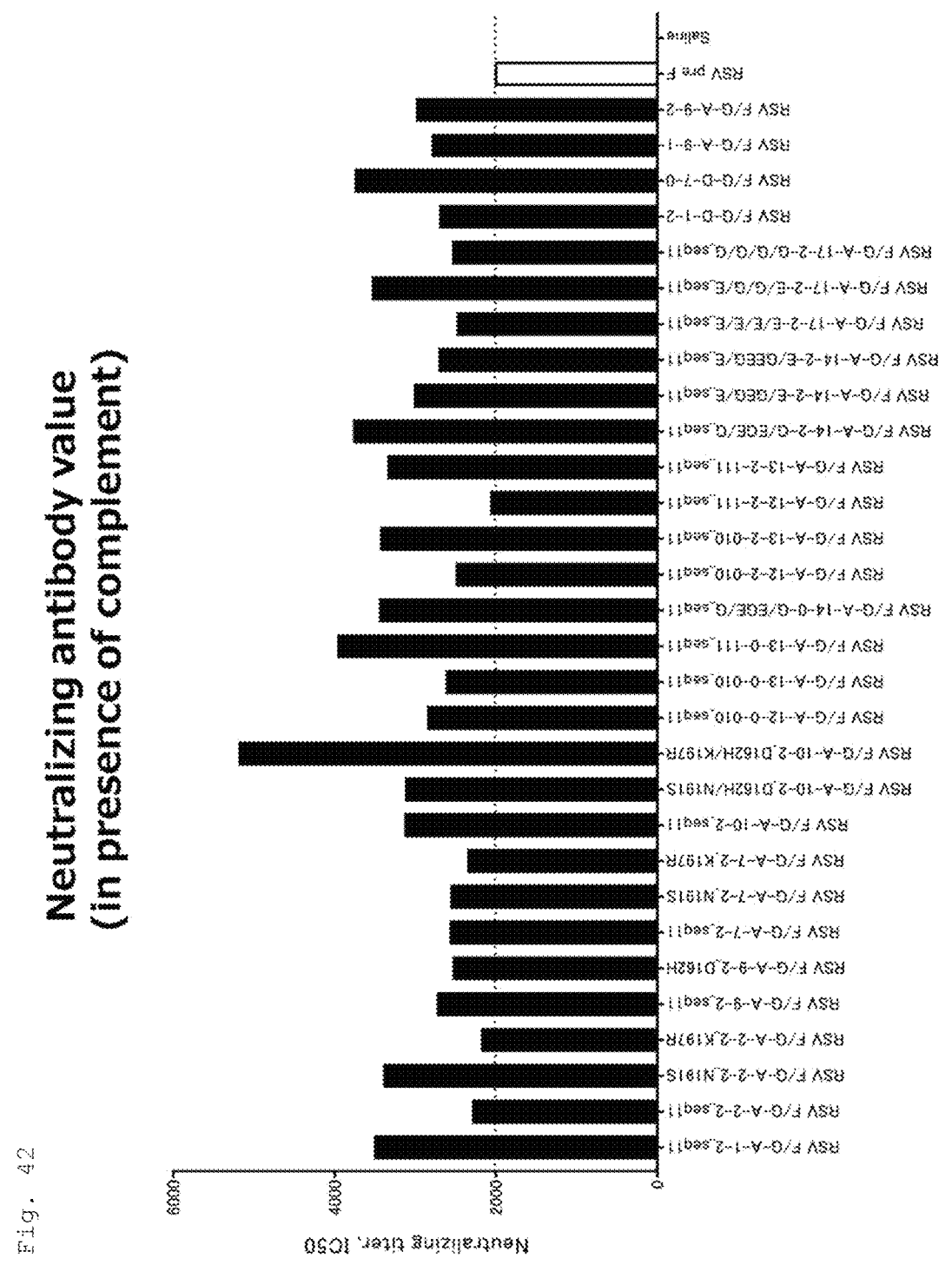

Serum of the administration group using Adju-Phos® was obtained in the same manner as in Example 4, and a complement-dependent neutralization test was carried out. As shown in FIG. 19, the neutralizing antibody titer (IC50, geometric mean) of RSV pre F tends to be high as compared with that of RSV F/G-A-9-1 and RSV F/G-A-9-2, but the neutralizing antibody titer (IC50, geometric mean) in the presence of complement shown in FIG. 20 resulted in higher in the RSV F/G-A-9-1 and the RSV F/G-A-9-2 than in the RSV pre F. (Dunn's multiple comparison test, *: $p<0.05$, n=5 to 8) In addition, as shown in FIG. 42, a large number of RSV F/G chimeric proteins having a high neutralizing antibody titer as compared with the RSV pre F were observed.

Example 6

Subclass Analysis

Figure 21:
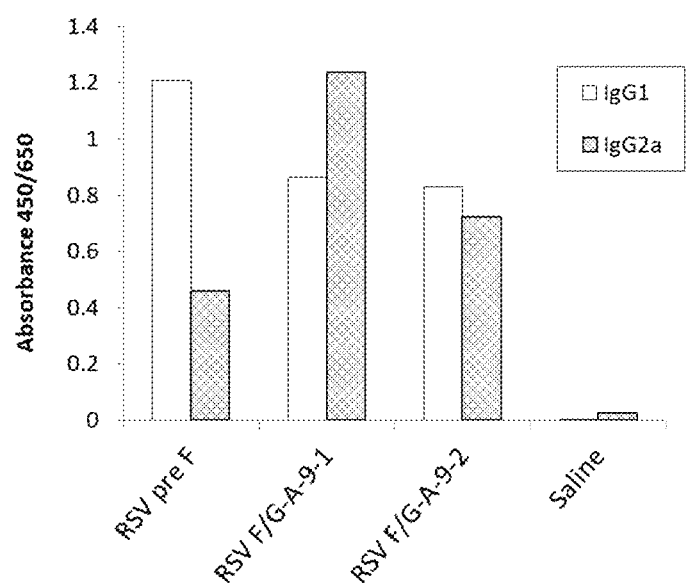
FIG. 21 shows the results of subclass analysis of anti-RSV F protein antibodies contained in RSV F/G chimeric protein immune sera.

Serum of the administration group using Adju-Phos® was obtained in the same manner as in Example 4 and Example 5, and subclass analysis of anti-RSV F antibodies present in the RSV pre F, RSV F/G-A-9-1, RSV F/G-A-9-2, and Saline immune serum was performed. The results of the subclass analysis are shown in FIG. 21. It was found that the RSV F/G-A-9-1 and the RSV F/G-A-9-2 had high inducibility of IgG2a with high complement-binding ability, whereas the RSV pre F had high inducibility of IgG1 without complement-binding ability.

Example 7

Evaluation of Inducibility of Anti-RSV G Antibody

Figure 22:
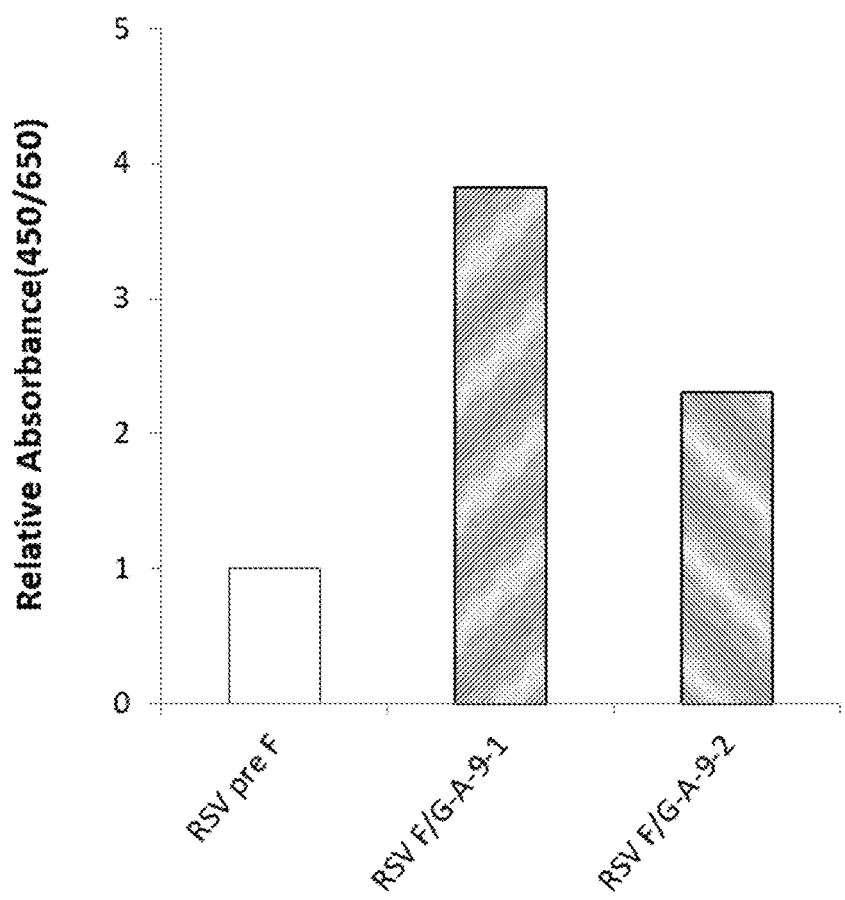
FIG. 22 shows an evaluation of an anti-RSV G protein antibody induced by immunization with RSV F/G chimeric proteins.

Serum of the administration group using Adju-Phos® was obtained in the same manner as in Example 4, Example 5 and Example 6, and inducibility of anti-RSV G antibody present in the RSV pre F, RSV F/G-A-9-1, RSV F/G-A-9-2, and Saline immune serum was evaluated. The evaluation results of inducibility of the anti-RSV G antibody are shown in FIG. 22. It was shown that an antibody having high reactivity with the RSV G protein was present in the RSV F/G-A-9-1 and RSV F/G-A-9-2 immune sera as compared with the RSV pre F immune serum, and it was suggested that the anti-RSV G antibody was induced by the RSV F/G-A-9-1 and the RSV F/G-A-9-2.

Example 8

Test in Protection Against Infection

Figure 23:
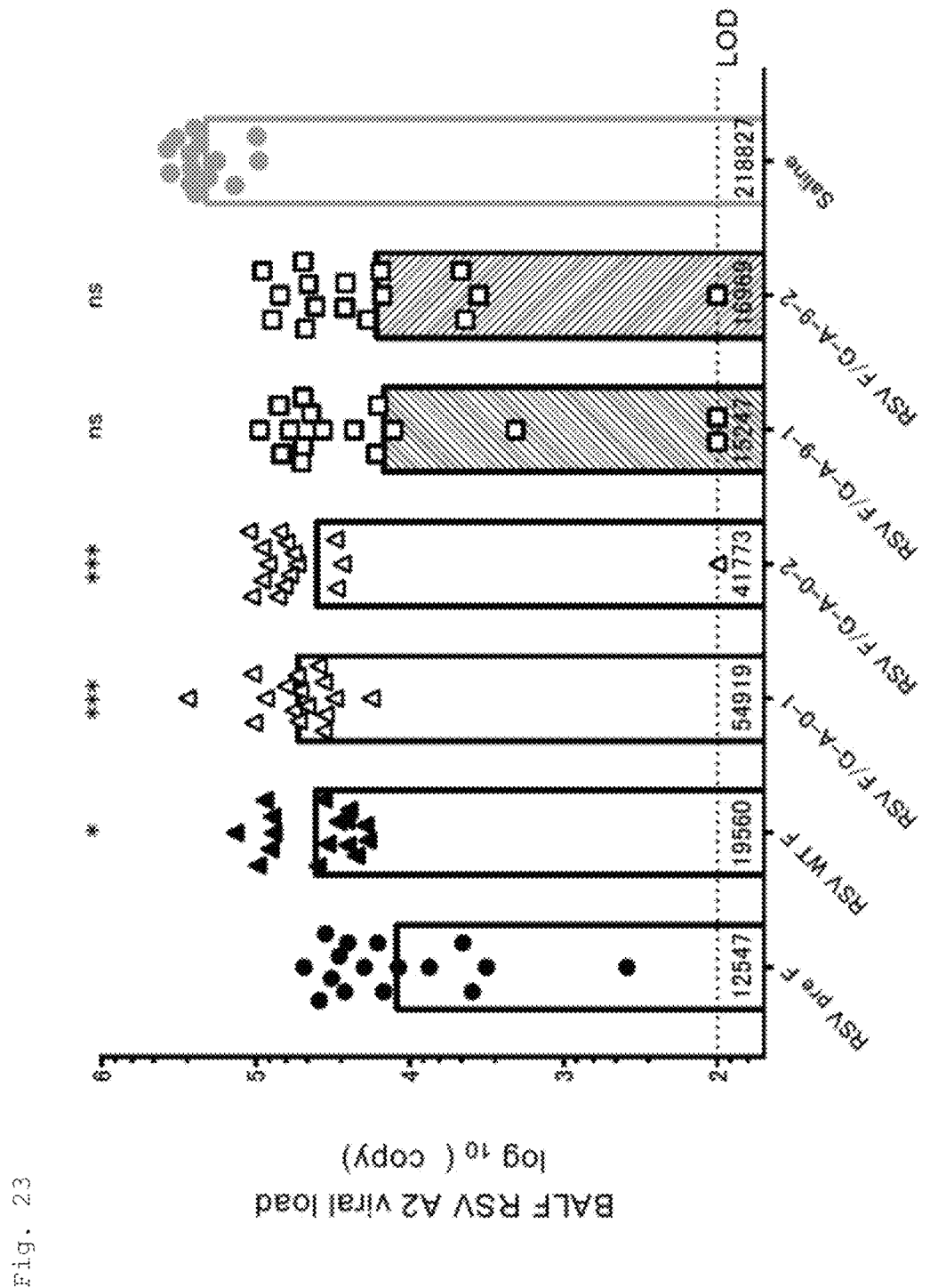
FIG. 23 shows the results of test in protection against infection of RSV F/G chimeric vaccines.
Figure 24:
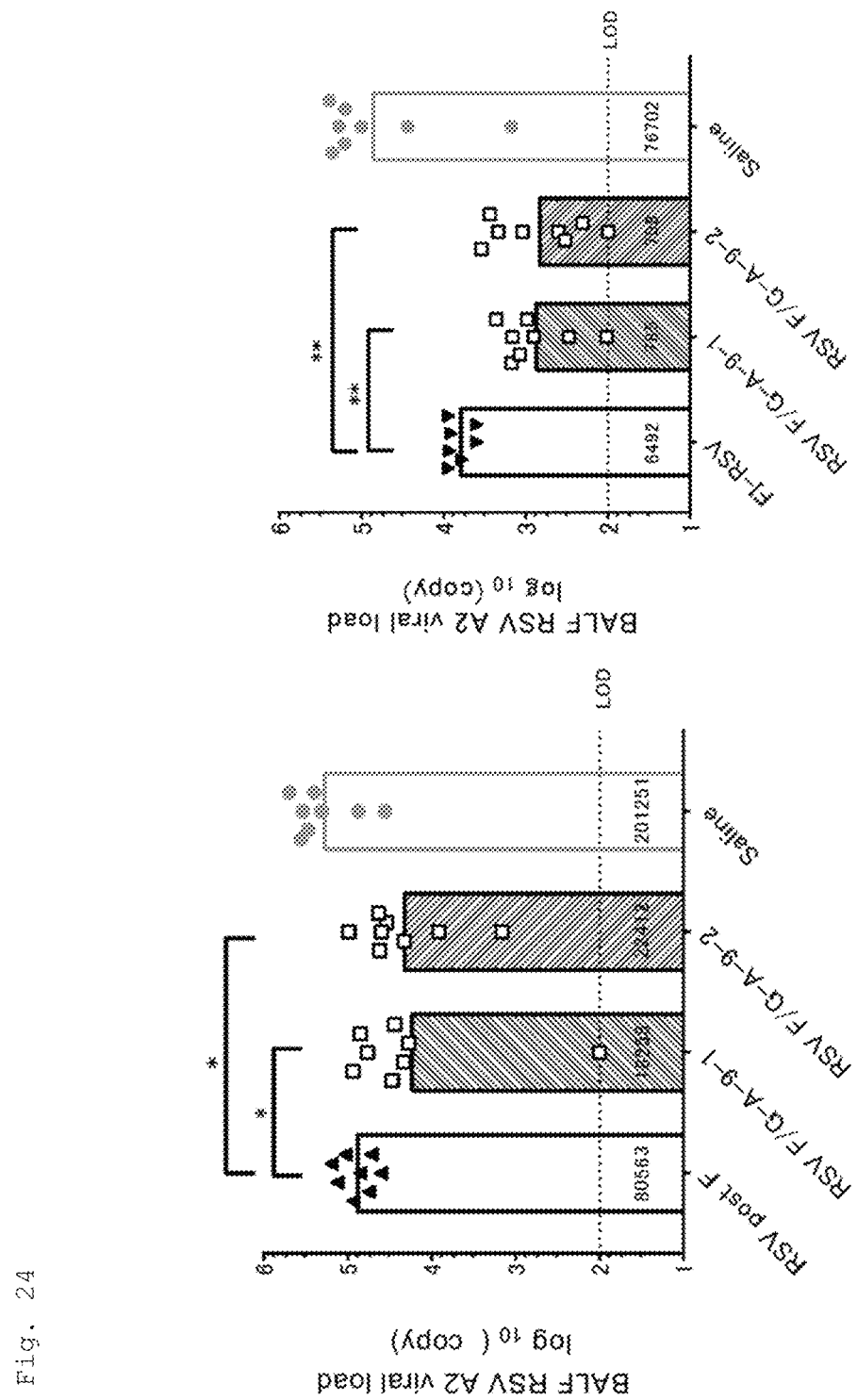
FIG. 24 shows the results of test in protection against infection of RSV F/G chimeric vaccines.

Each protein was prepared to 5 μg/mouse/time (no adjuvant), and 6-week-old female BALB/c mice were immunized twice at intervals of 3 weeks, and infected with RSV after weeks. Three days after RSV inoculation, BALF was collected, RNA extraction and cDNA synthesis were performed, and viral copy number (geometric mean) was quantified using real-time PCR. The results of infection protection test of RSV pre F, RSV WT F, RSV F/G-A-0-1 and RSV F/G-A-0-2, and RSV F/G-A-9-1 and RSV F/G-A-9-2 are shown in FIG. 23. Since the RSV F/G-A-9-1 and the RSV F/G-A-9-2 showed viral copy number comparable to that of the RSV pre F, it was suggested that they had infection protective ability comparable to that of the RSV pre F. In addition, it was suggested that the copy numbers of the RSV F/G-A-9-1 and the RSV F/G-A-9-2 were low as compared with those of the RSV WT F, RSV F/G-A-0-1, and RSV F/G-A-0-2 comprising no RSV G protein sequence, and the infection protective ability tends to be high (vs RSV pre F; Dunn's multiple comparison test, ***: $p<0.002$, *: $p<0.05$, n=14 to 16). A comparison result with RSV post F is shown in FIG. 24 (left), and a comparison result with FI-RSV is shown in FIG. 24 (right). In comparison with RSV post F, the test was performed under an immune condition of 15 μg/mouse/time, and significant reduction in viral copy number was observed in the RSV F/G-A-9-1 and the RSV F/G-A-9-2 as compared with the RSV post F (Dunn's multiple comparison test, ***: $p<0.002$, *: $p<0.05$, n=8). In comparison with FI-RSV, the test was performed under an immune condition of 5 μg/mouse/time, and significant reduction in viral copy number was observed in the RSV F/G-A-9-1 and the RSV F/G-A-9-2 as compared with the FI-RSV (Dunn's multiple comparison test, **: $p<0.01$, *: $p<0.05$, n=7 to 8).

Example 9

Figure 25:
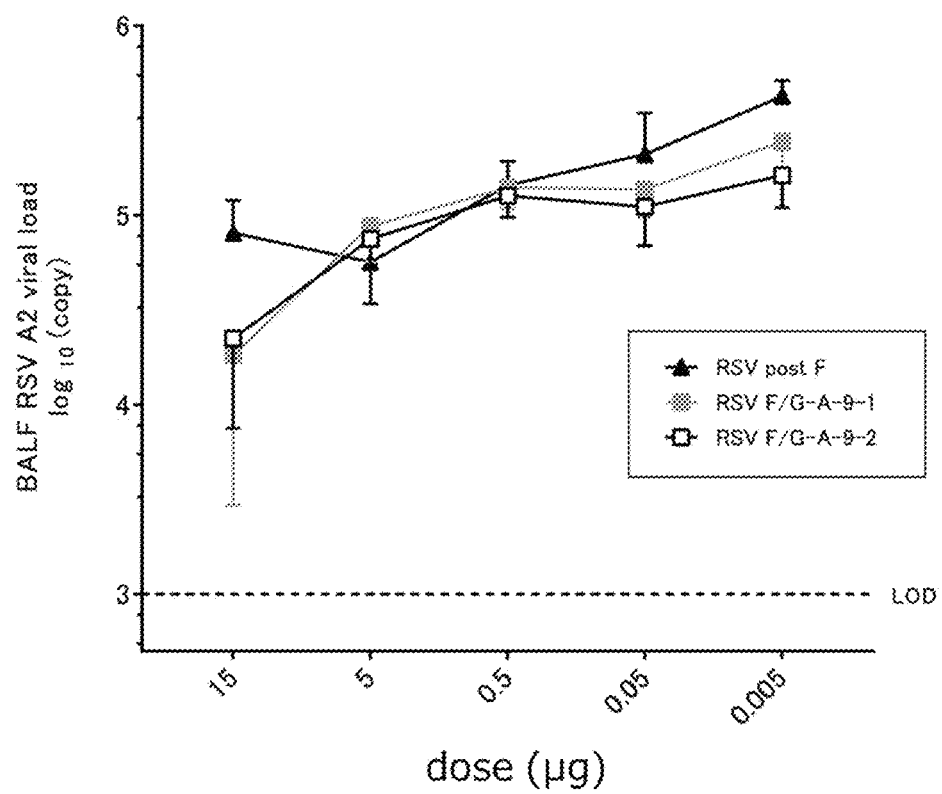
FIG. 25 shows the results of test in protection against infection of RSV F/G chimeric vaccines.

In order to confirm dose dependence, viral copy number (geometric mean) in BALF was measured by setting immune conditions of RSV post F, RSV F/G-A-9-1, and RSV F/G-A-9-2 to 5 doses of 15, 5, 0.5, 0.05, and 0.005 μg/mouse, in the same manner as in Example 8 for other conditions, and the results are shown in FIG. 25. It was shown that the viral copy number of the RSV post F did not change at 5 μg/mouse and 15 μg/mouse, the viral copy numbers of the RSV F/G-A-9-1 and the RSV F/G-A-9-2 were lower than that of the RSV post F in the high dose range (15 μg/mouse), the infection protective ability exceeded that of the RSV post F, and the infection protective ability of the RSV F/G-A-9-1 and the RSV F/G-A-9-2 exceeded that of the RSV post F also in the low dose range (0.05, 0.005 μg/mouse). Therefore, it was suggested that maximum efficacy of the RSV F/G-A-9-1 and the RSV F/G-A-9-2 exceeded that of the RSV post F, and efficacy at minimum dose also exceeded that of the RSV post F (error bar: 95% confidence interval, n=8).

Example 10

Evaluation of Infection Suppressing Ratio

Figure 26:
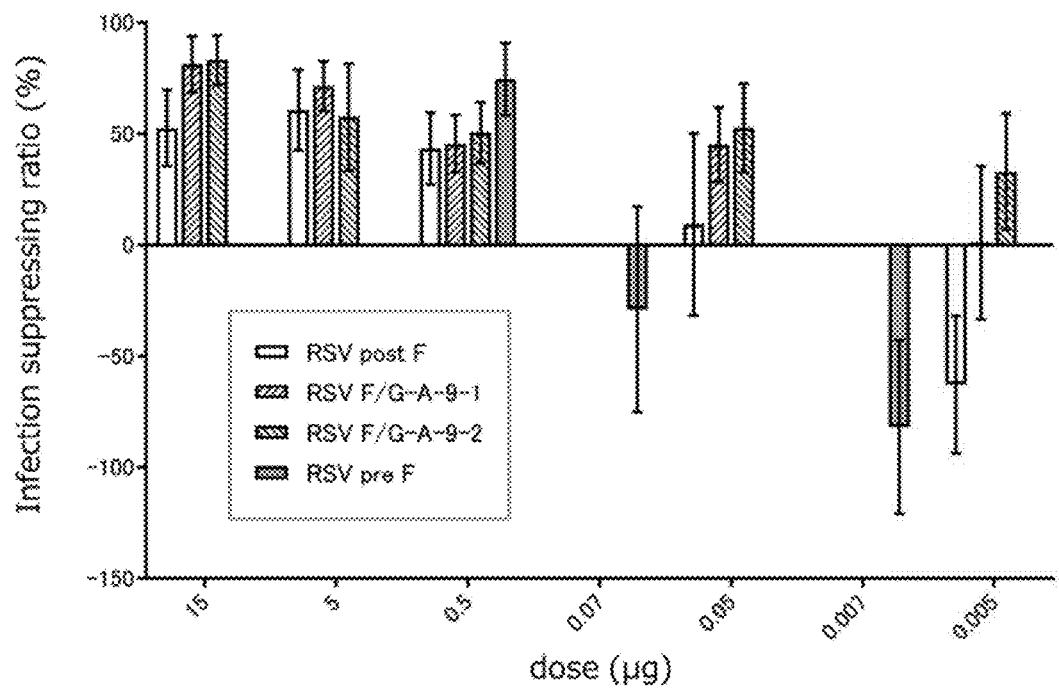
FIG. 26 shows the results of evaluating infection suppressing ratios of RSV F/G chimeric vaccines.
Figure 27:
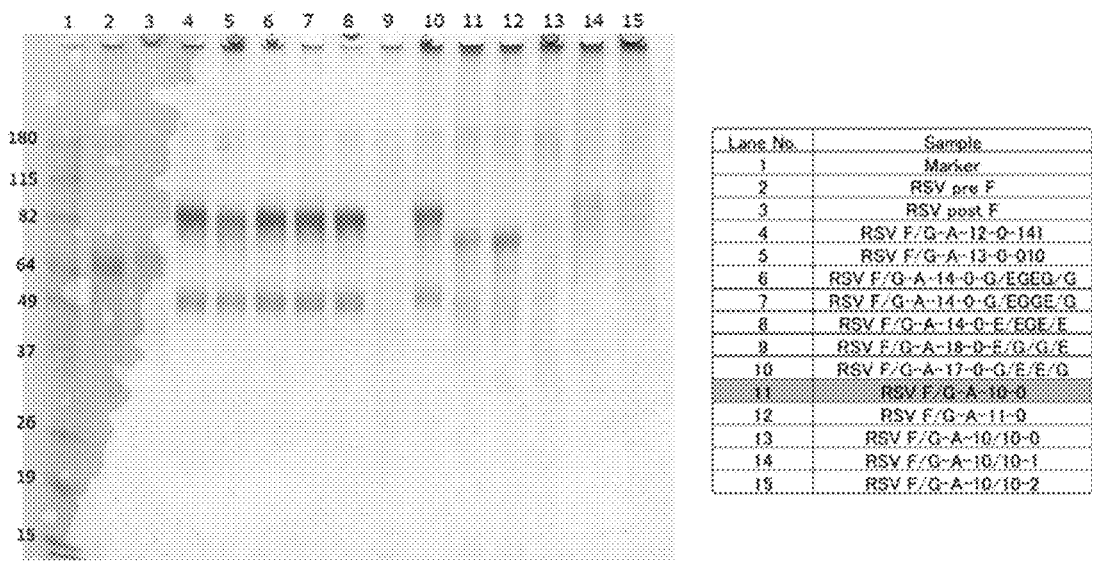
FIG. 27 shows the results of SDS-PAGE of RSV F/G chimeric proteins.
Figure 30:
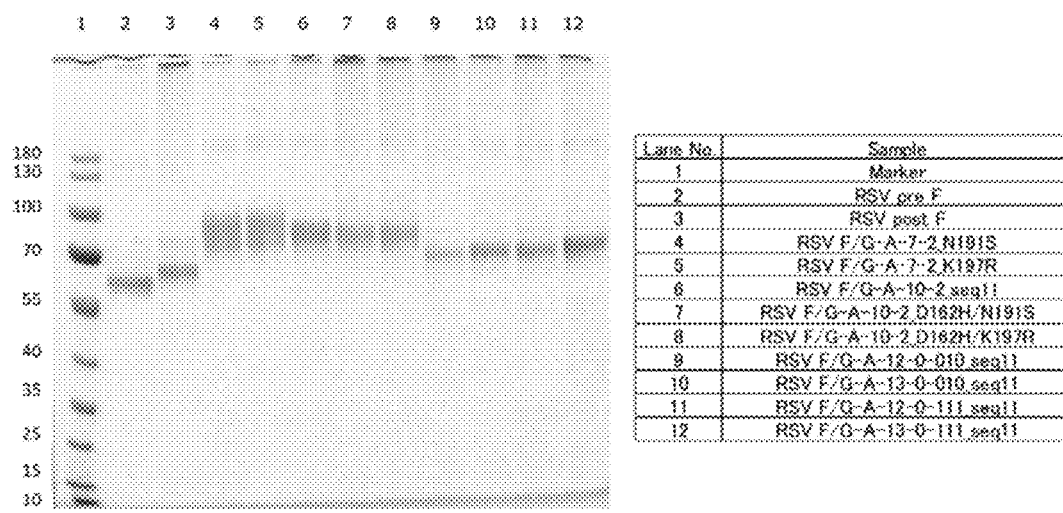
FIG. 30 shows the results of SDS-PAGE of RSV F/G chimeric proteins.
Figure 31:
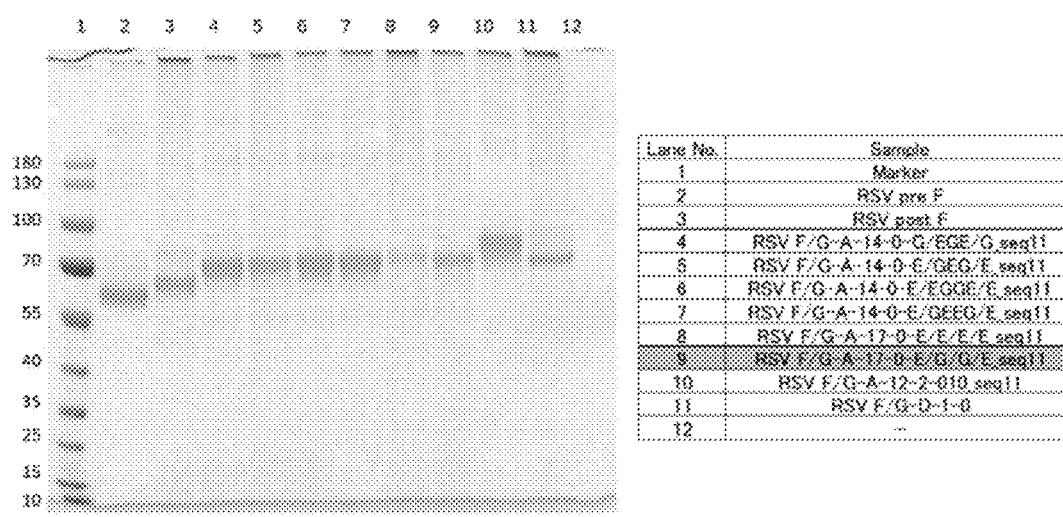
FIG. 31 shows the results of SDS-PAGE of RSV F/G chimeric proteins.
Figure 32:
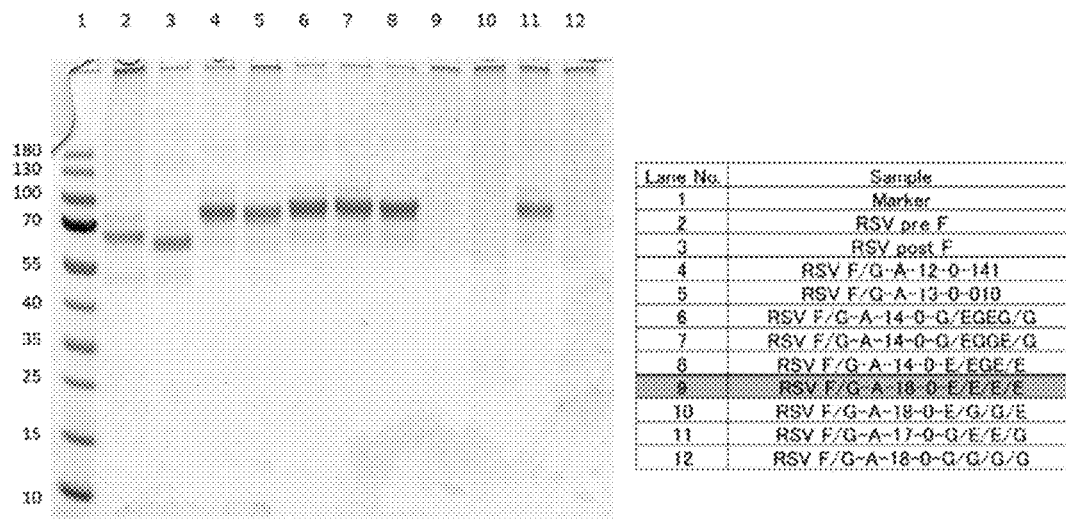
FIG. 32 shows the results of SDS-PAGE of RSV F/G chimeric proteins.
Figure 33:
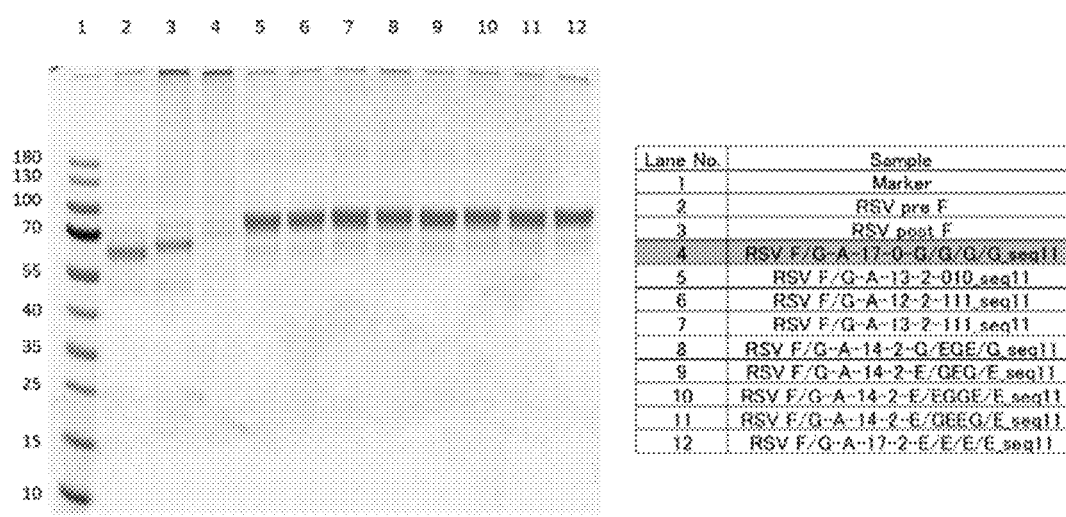
FIG. 33 shows the results of SDS-PAGE of RSV F/G chimeric proteins.
Figure 38:
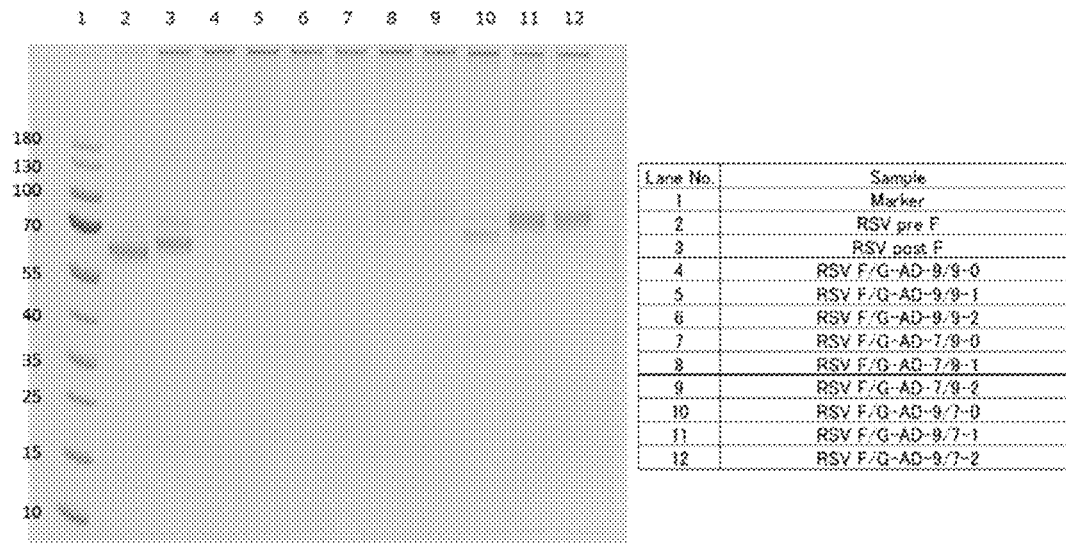
FIG. 38 shows the results of SDS-PAGE of RSV F/G chimeric proteins.
Figure 39:
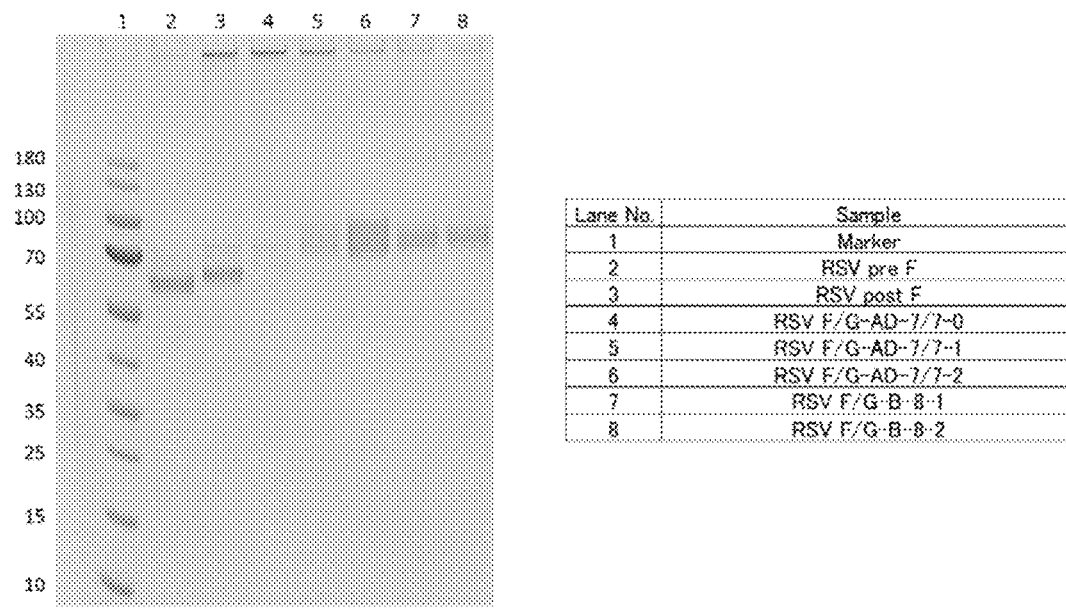
FIG. 39 shows the results of SDS-PAGE of RSV F/G chimeric proteins.

From the results of test in protection against infection, infection suppressing ratios of RSV F/G-A-9-1, RSV F/G-A-9-2, RSV post F, and RSV pre F were calculated based on the viral copy number (geometric mean) of the Saline group (control group not immunized with antigen) (performed under immune conditions of RSV F/G-A-9-1, RSV F/G-A-9-2 and RSV post F at 5 doses of 15, 5, 0.5, 0.05 and 0.005 μg/mouse, and immune conditions of RSV pre F at 3 doses of 0.5, 0.08 and 0.008 μg/mouse). The calculation results of infection suppressing ratio are shown in FIG. 26. When a low dose immunization group was set to confirm exacerbation tendency, as compared with the viral copy number of Saline, a high viral copy number was detected at 0.08 μg/mouse or less in the RSV pre F and 0.005 μg/mouse in the RSV post F was detected, and enhancement of infection tendency was shown. On the other hand, in the RSV F/G-A-9-1 and the RSV F/G-A-9-2, no enhancement of infection tendency was observed. (error bar: 95% confidence interval, n=4 to 8)

Example 11

Evaluation of Infection Enhancement

Figure 43:
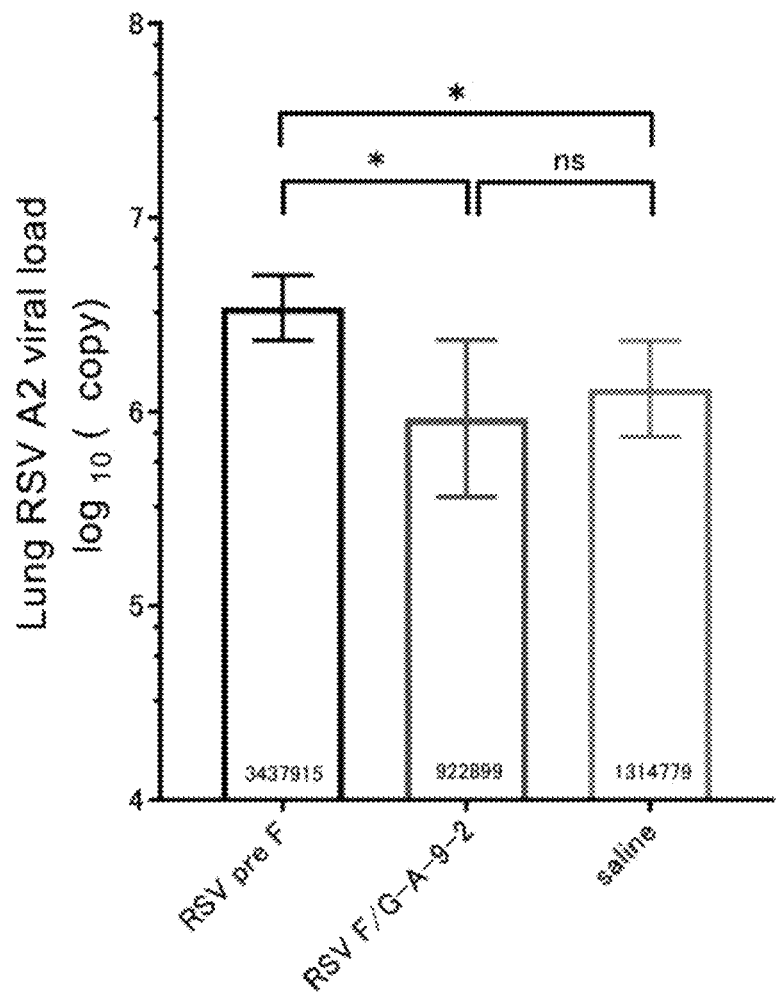
FIG. 43 shows the results of evaluating infection enhancement of RSV F/G chimeric vaccines.

Immune sera were transferred to evaluate enhancement of infection after passive immunization. As shown in FIG. 43, enhancement of infection was significantly observed in the RSV preF, but enhancement of infection was not observed in the RSV F/G-A-9-2. (Dunn's multiple comparison test, *: $p<0.05$, error bars: 95% confidence interval, n=13).

INDUSTRIAL APPLICABILITY

The present invention is useful in the field of pharmaceuticals, particularly in the field of vaccines.

---

The invention claimed is:

1. A chimeric protein (RSV F/G protein) of Respiratory Syncytial Virus (RSV) F protein and G protein, the chimeric protein comprising an amino acid sequence of the RSV F protein having an identity of 90% or more to the amino acid sequence of SEQ ID NO: 1 (the RSV F protein), and a portion of CCD sequence of RSV G protein,
   wherein a portion of the RSV F protein is replaced with a portion of CCD sequence of RSV G protein or wherein a portion of CCD sequence of RSV G is added to the RSV F protein,
   the RSV F protein is composed of sites including an SP domain, an F2 domain, a p27 domain, an FP domain, an F1 domain, in order from an N-terminus, and
   wherein the portion of the RSV F protein that is replaced with a portion of CCD sequence of RSV G protein is selected from the group consisting of positions 137 to 146 of SEQ ID NO: 1; positions 382 to 393 of SEQ ID NO: 1; and positions 425 to 436 of SEQ ID NO: 1; and wherein:
   (1) the portion of the CCD sequence to be replaced or added comprises a sequence selected from the group consisting of a sequence at positions 162 to 171 of SEQ ID NO: 2, a sequence at positions 187 to 197 of SEQ ID NO: 2, a sequence in which sequences at positions 162 to 172 and at positions 187 to 199 of SEQ ID NO: 2 are linked, a sequence in which sequences at positions 164 to 172 and at positions 187 to 197 of SEQ ID NO: 2 are linked, a sequence in which sequences at positions 162 to 172, at positions 187 to 199 and at positions 162 to 172 of SEQ ID NO: 2 are linked, and a sequence in which two or three of a sequence at positions 162 to 172 of SEQ ID NO: 2 are linked, or
   (2) the portion of the CCD sequence to be replaced or added comprises a sequence selected from the group consisting of a sequence at positions 162 to 171 of SEQ ID NO: 11 of RSV G protein, a sequence at positions 164 to 172 of SEQ ID NO: 11 of RSV G protein, and a sequence at positions 187 to 197 of SEQ ID NO: 11 of RSV G protein, a sequence in which sequences at positions 162 to 172 and at positions 187 to 197 of SEQ ID NO: 11 are linked, a sequence in which sequences at positions 164 to 172 and at positions 187 to 197 of SEQ ID NO: 11 are linked, a sequence in which sequences at positions 162 to 172 and at positions 187 to 199 of SEQ ID NO: 11 are linked, and a sequence in which two or three of a sequence at positions 162 to 172 of SEQ ID NO: 11 are linked.

2. The chimeric protein of claim 1, the portion of the RSV F protein is replaced with RSV G protein at positions 162 to 171 of SEQ ID NO: 2 or wherein RSV G protein at positions 162 to 171 is added to RSV F protein.

3. The chimeric protein of claim 1, wherein a portion of FP domain of the RSV F protein is replaced with RSV G protein at positions 162 to 171 of SEQ ID NO: 2.

4. The chimeric protein of claim 1, wherein the sequence of RSV F protein corresponding to the amino acid sequence at positions 137 to 146 of SEQ ID NO: 1 is replaced with RSV G protein at positions 162 to 171 of SEQ ID NO: 2.

5. The chimeric protein of claim 1, wherein RSV G protein at positions 162 to 171 of SEQ ID NO: 2 is added to the C-terminal of the RSV F protein.

6. The chimeric protein of claim 1, wherein the portion of RSV F protein that is replaced with the portion of CCD sequence of RSV G protein is replaced with RSV G protein at positions 187 to 197 of SEQ ID NO: 2 or wherein RSV G protein at positions 187 to 197 is added to the RSV F protein.

7. The chimeric protein of claim 1, wherein a portion of FP domain of the RSV F protein is replaced with RSV G protein at positions 187 to 197 of SEQ ID NO: 2.

8. The chimeric protein of claim 1, wherein the sequence of RSV F protein corresponding to the amino acid sequence at positions 137 to 146 of SEQ ID NO: 1 is replaced with RSV G protein at positions 187 to 197 of SEQ ID NO: 2.

9. The chimeric protein of claim 1, wherein RSV G protein at positions 187 to 197 of SEQ ID NO: 2 is added to the C-terminal of the RSV F protein.

10. The chimeric protein of claim 1, wherein a portion of FP domain of the RSV F protein is replaced with a sequence in which RSV G protein at positions 162 to 172 of SEQ ID NO: 2 and a sequence at positions 187 to 199 are linked via a linker.

11. The chimeric protein of claim 1, wherein a portion of FP domain of the RSV F protein is replaced with a sequence in which RSV G protein at positions 162 to 172 of SEQ ID NO: 2 and a sequence at positions 187 to 199 are linked via a linker of GGGGS (SEQ ID NO: 5) or EAAAK (SEQ ID NO: 6).

12. The chimeric protein of claim 1, wherein a sequence in which RSV G protein at positions 162 to 172 of SEQ ID NO: 2 and a sequence at positions 187 to 199 are linked via a linker is added to the C-terminal of the RSV F protein.

13. The chimeric protein of claim 1, wherein a sequence in which RSV G protein at positions 162 to 172 of SEQ ID NO: 2 and a sequence at positions 187 to 199 are linked via a linker of GGGGS (SEQ ID NO: 5) or EAAAK (SEQ ID NO: 6) is added to the C-terminal of the RSV F protein.

14. The chimeric protein of claim 1, wherein a portion of FP domain of the RSV F protein comprising the amino acid sequence of SEQ ID NO: 1 is replaced with a sequence in which RSV G protein at positions 162 to 172 of SEQ ID NO: 2 and a sequence at positions 187 to 199 are linked.

15. The chimeric protein of claim 1, wherein a sequence in which RSV G protein at positions 162 to 172 of SEQ ID NO: 2 and a sequence at positions 187 to 199 are linked is added to the C-terminal of the RSV F protein comprising the amino acid sequence of SEQ ID NO: 1.

16. The chimeric protein of claim 1, wherein the sequence of RSV F protein corresponding to the amino acid sequence at positions 137 to 146 of SEQ ID NO: 1 is replaced with RSV G protein at positions 162 to 171, and amino acid modifications of K419N, K421T, and G430T are made in F protein.

17. The chimeric protein of claim 1, wherein the sequence of RSV F protein corresponding to the amino acid sequence at positions 137 to 146 of SEQ ID NO: 1 is replaced with RSV G protein at positions 162 to 171, and amino acid modifications of K419N, K421T, and T434N and S436T are made in F protein.

18. The chimeric protein of claim 1, wherein a glycosylation site is introduced into the vicinity of siteIV of the RSV F protein at positions 419 to 468 of SEQ ID NO: 1 by an amino acid modification, and the amino acid modification for introduction of the glycosylation site is the following (1) or (2):
 (1) K419N, K421T, and G430T
 (2) K419N, K421T, and T434N and S436T.

19. The chimeric protein of claim 18, wherein the amino acid modification for introduction of the glycosylation site of siteIV of the RSV F protein is K419N, K421T, and G430T.

20. The chimeric protein of claim 18, wherein the amino acid modification for introduction of the glycosylation site of siteIV of the RSV F protein is K419N, K421T, and T434N and S436T.

21. An immunogenic composition comprising as an antigen the chimeric protein of claim 1.

22. The immunogenic composition of claim 21, wherein the immunogenic composition has a lower exacerbation tendency of RSV infection than RSV F protein, wherein the CCD sequence of protein G excludes a cysteine noose (amino acids 173-186 of SEQ ID NO: 2).

23. The immunogenic composition of claim 21, wherein the immunogenic composition has a higher complement-dependent neutralization titer than that of RSV F protein.

24. A DNA fragment coding for the chimeric protein of claim 1.

25. An expression vector comprising the DNA fragment of claim 24.

26. An isolated cell transfected with the DNA fragment of claim 24.

27. An isolated cell transfected with the expression vector of claim 25.

* * * * *